US006792308B2

(12) United States Patent
Corbucci

(10) Patent No.: US 6,792,308 B2
(45) Date of Patent: Sep. 14, 2004

(54) MYOCARDIAL PERFORMANCE ASSESSMENT

(75) Inventor: Giorgio Corbucci, Crevalcore (IT)

(73) Assignee: Medtronic, Inc., Minneapolis, MN (US)

(*) Notice: Subject to any disclaimer, the term of this patent is extended or adjusted under 35 U.S.C. 154(b) by 301 days.

(21) Appl. No.: 10/001,148

(22) Filed: Nov. 15, 2001

(65) Prior Publication Data

US 2002/0151938 A1 Oct. 17, 2002

Related U.S. Application Data

(60) Provisional application No. 60/248,587, filed on Nov. 17, 2000.

(51) Int. Cl.[7] ............................................. A61N 1/365

(52) U.S. Cl. ........................ 607/17; 607/18; 607/25; 600/514

(58) Field of Search .................... 600/509, 514, 600/528; 607/9, 17, 18, 25

(56) References Cited

U.S. PATENT DOCUMENTS

| 4,316,472 A | 2/1982 | Mirowski et al. ............... 607/9 |
|---|---|---|
| 4,375,817 A | 3/1983 | Engle et al. .................... 607/4 |
| 4,379,459 A | 4/1983 | Stein ............................. 607/9 |
| 4,384,585 A | 5/1983 | Zipes ............................ 607/5 |
| 4,476,868 A | 10/1984 | Thompson .................... 607/14 |
| 4,556,063 A | 12/1985 | Thompson et al. ............ 607/32 |
| 4,577,633 A | 3/1986 | Berkowitz et al. ............ 607/15 |
| 4,587,970 A | 5/1986 | Holley et al. ................. 607/15 |
| 4,726,380 A | 2/1988 | Vollmann et al. ............. 607/15 |
| 4,727,877 A | 3/1988 | Kallok ........................... 607/5 |
| 4,763,646 A | 8/1988 | Lekholm ...................... 607/14 |
| 4,800,883 A | 1/1989 | Winstrom ....................... 607/7 |
| 4,821,723 A | 4/1989 | Baker, Jr. et al. ............... 607/7 |
| 4,830,006 A | 5/1989 | Haluska et al. ................ 607/4 |
| 4,880,005 A | 11/1989 | Pless et al. ................... 607/15 |
| 4,949,719 A | 8/1990 | Pless et al. ..................... 607/7 |
| 4,953,551 A | 9/1990 | Mehra et al. .................. 607/5 |
| 5,117,824 A | 6/1992 | Keimel et al. ................. 607/4 |
| 5,131,388 A | 7/1992 | Pless et al. .................... 607/5 |
| 5,144,949 A | 9/1992 | Olson .......................... 607/17 |
| 5,158,078 A | 10/1992 | Bennett et al. ............... 607/27 |

(List continued on next page.)

FOREIGN PATENT DOCUMENTS

| WO | WO 92/18198 | 10/1992 | ............ A61N/1/39 |

OTHER PUBLICATIONS

Wood et al., "Regional Effects of Myocardial Ischemia on Epicardially Recorded Canine First Heart Sound," J Appl. Physiol 76(1) pp. 291–302, 1994.
Salerno et al., "Seismocardiography: A New Technique for Recording Cardiac Vibrations. Concept, Method, and Initial Observations," J Cardiovasc Tech, vol. 9, N 2, pp. 111–118, 1990.
Weissler et al., "Systolic Time Intervals in Heart Failure in Man," Circulation, vol. 37, pp. 149–159, 1968.

(List continued on next page.)

Primary Examiner—Carl H. Layno
(74) Attorney, Agent, or Firm—Daniel G. Chapik; Girma Wolde-Michael

(57) ABSTRACT

Myocardial performance is assessed using a combination of electrical and mechanical criteria. More specifically, this assessment may be based on a QT interval based on electrogram (EGM) readings and on first and second heart sounds. The timing relationships between the QT interval and the first and second heart sounds can be used to evaluate certain systolic, diastolic, and systolic/diastolic parameters relating to myocardial performance. In addition, these parameters may be used to automatically drive therapies. For example, myocardial performance parameters obtained from the QT interval and from the timing of the first and second heart sounds may be used to optimize the AV delay and to optimize multisite pacing.

50 Claims, 12 Drawing Sheets

U.S. PATENT DOCUMENTS

| | | | | |
|---|---|---|---|---|
| 5,163,427 | A | 11/1992 | Keimel | 607/5 |
| 5,188,105 | A | 2/1993 | Keimel | 607/5 |
| 5,199,428 | A | 4/1993 | Obel et al. | 607/44 |
| 5,207,218 | A | 5/1993 | Carpentier et al. | 607/36 |
| 5,269,298 | A | 12/1993 | Adams et al. | 607/5 |
| 5,312,453 | A | 5/1994 | Shelton et al. | 607/19 |
| 5,314,430 | A | 5/1994 | Bardy | 607/5 |
| 5,330,507 | A | 7/1994 | Schwartz | 607/14 |
| 5,331,966 | A | 7/1994 | Bennett et al. | 600/508 |
| 5,334,222 | A | 8/1994 | Salo et al. | 607/17 |
| 5,354,316 | A | 10/1994 | Keimel | 607/15 |
| 5,496,351 | A | 3/1996 | Plicchi et al. | 607/17 |
| 5,540,727 | A | 7/1996 | Tockman et al. | 607/18 |
| 5,545,186 | A | 8/1996 | Olson et al. | 607/14 |
| 5,554,177 | A | 9/1996 | Kieval et al. | 607/17 |
| 5,584,868 | A | 12/1996 | Salo et al. | 607/17 |
| 5,690,686 | A | 11/1997 | Min et al. | 607/5 |
| 5,700,283 | A | 12/1997 | Salo | 607/17 |
| 5,800,465 | A | 9/1998 | Thompson et al. | 607/9 |
| 6,188,927 | B1 * | 2/2001 | Lu et al. | 607/17 |
| 6,314,322 | B1 * | 11/2001 | Rosenberg | 607/17 |

OTHER PUBLICATIONS

Rickards et al., "An Implantable Intracardiac Accelerometer for Monitoring Myocardial Contractility," PACE, vol. 19, pp. 2066–2071, 1996.

Plicchi et al., "PEA I and PEA II Based Implantable Heamodynamic Monitor: Pre–clinical Studies in Sheep," NASPE 2000, abstract 432.

Step et al., "Effect of Altering P–R Interval on the Amplitude of the First Heart Sound in the Anesthetized Dogs," Circulation Research, vol. 25, pp. 255–263, 1969.

Wexler et al., "The Relationship of the First Heart Sound to Mitral Valve Closure in Dogs," Circulation 66, N.1, pp. 235–243, 1982.

Ritter et al., "Determination of the Optimal Atrioventricular Delay in DDD Pacing," Europace, N.1., pp. 126–130, 1999.

The Heard Sounds, Braunwald "Heart Disease" $5^{th}$ Edition, 29 Ch 2.

Auricchio et al., "Effect of Pacing Chamber and Atrioventricular Delay on Acute Systolic Function of Paced Patients with Congestive Heart Failure," Circulation. 99, pp. 2993–3001, 1999.

Kass et al., "Improved Left Ventricular Mechanics from Acute VDD Pacing in Patients with Dilated Cardiomyopathy and Ventricular Conduction Delay," Circulation. 99, pp. 1567–1573, 1999.

Auricchio et al., "LV dP/dt Predicts Mortality in PATH–CHF Trial," NASPE 2000, abstract 511.

Saxon et al., "Chronic Biventricular Pacing Improves Indices of Systolic Function and Reduces Left Ventricular Volume," NSAPE 2000, abstract 331.

Dujardin et al., "Prognostic Value of a Doppler Index Combining Systolic and Diastolic Performance in Idiopathic–Dilated Cardiomvopathy," Am J Cardiol, 82, pp. 1071–1076, 1998.

Ruiter et al., "Adaptive Rate Pacing Controlled by the RV Preejection Interval: Cllinical Experience with a Physiological Pacing System," PACE, vol. 15, pp. 886–894, 1999.

Clinical Cardiac Pacing and Defibrillation. Ellenborgen, Kay, Vilkoff. $2^{nd}$ Edition. p. 300.

Clinical Cardiac Pacing and Defibrillation. Ellenborgen, Kay, Vilkoff. $2^{nd}$ Edition. p. 316.

Olson et al., "Onset and Stability for Ventricular Tachyarrhythmia Detection in an Implantable Pacer–Cardioverter–Defibrillator," Computers in Cardiology, IEEE Computer Society Press, pp. 167–170, 1986.

Arzbaecher et al., "Automatic Tachycardia Recognition," PACE, pp. 541–547, 1984.

* cited by examiner

MYOCARDIAL PERFORMANCE ASSESSMENT

CROSS-REFERENCE TO RELATED APPLICATION

This application claims priority to U.S. Provisional Patent Application No. 60/248,587, filed Nov. 17, 2000, the entirety of which is incorporated herein by reference.

FIELD OF THE INVENTION

The present invention relates to cardiac pacemakers, and more specifically to evaluation of myocardial performance in connection with cardiac pacemakers.

BACKGROUND

Cardiac pacemakers play an important role in the treatment of patients suffering from heart failure. Pacemakers can be single-chamber or multi-chamber pacemakers. A single-chamber pacemaker delivers pacing pulses to one heart chamber to maintain a normal heart rhythm. Multi-chamber pacemakers deliver pacing pulses to multiple chambers. For example, dual-chamber pacemakers deliver pacing pulses to two heart chambers, e.g., the right atrium and the right ventricle, or the left and right ventricles. In a bi-ventricular pacing system, for example, a right ventricular pacing lead is positioned in the right ventricle of the heart and a left ventricular pacing lead is positioned via the coronary sinus in a cardiac vein, such as the middle or great cardiac vein. These pacing leads sense electrical activity that may be indicative of cardiac activity, such as ventricular contraction. The pacing leads also supply pacing pulses, i.e., electrical impulses that cause the heart to contract.

The timing of pacing pulses is often important. Many patients benefit from having chambers paced in a particular order with a delay between the respective pacing pulses. For example, in dual-chamber pacing, the length of time between an atrial sensed or atrial paced event and the delivery of a ventricular pacing pulse is known as the atrioventricular (AV) interval or AV delay. The optimal AV delay varies from patient to patient and may be determined using a number of techniques for evaluating cardiac performance, i.e., the efficiency of the heart as a pump. Assessments of cardiac performance may also be used in multisite pacing optimization.

Early cardiac performance assessment techniques focused on evaluating the performance of the right ventricle to realize a physiologic rate responsive function. With the increasing use of pacemakers to treat heart failure, however, it has become desirable to evaluate the performance of the left ventricle as well. Assessment of left ventricular performance is useful for monitoring the progression of heart disease, as well as for automatically driving electrical and drug therapies.

Some approaches have proposed estimating left ventricular performance based on measurements of right ventricular performance. For example, one commonly used parameter for evaluating cardiac performance is dynamic (or relative) pressure, dP/dt max, which is used to estimate contractility. In a normal heart, right ventricular dynamic pressure provides a reasonably accurate estimate of left ventricular dynamic pressure, but only for purposes of assessing contractility variations. Right ventricular dynamic pressure cannot be used to estimate absolute values of left ventricular dynamic pressure. In a failing heart, for example, the right ventricle may be normal and the left ventricle may be dilated, in which case the dynamics of dP/dt max in the right ventricle may not be the same as dP/dt max in the left ventricle. In addition, long-term reliability of implanted pressure sensors for measuring dynamic pressure has not yet been determined. Several months after implantation, fibrosis around the lead encapsulates the flexible membrane of the pressure sensor. This encapsulation may adversely affect the long-term reliability of the pressure sensor.

Right ventricular performance can also be assessed, for example, by estimating right ventricular stroke volume and pre-ejection interval (PEI) based on changes in impedance. In patients with heart failure, however, the heart can have a normal right ventricle and a dilated left ventricle. As a result, right ventricular performance may not be a reliable indicator of left ventricular performance.

Left ventricular performance can also be estimated by measuring endocardial acceleration. In particular, the peak endocardial acceleration (PEA) measures the amplitude of the first heart sound (FHS) as endocardially detected by a microaccelerometer in the tip of the pacing lead. It is well known that the first heart sound is affected both by left ventricular contractility and by the P-R interval. Consequently, an increase in the PEA may be attributable to an increase in contractility or to a decrease of the P-R interval. In other words, an increased amplitude of the first heart sound can indicate either good performance, i.e., increased contractility, or an AV delay that is too short, producing a short P-R interval. Amplitude assessment alone is therefore insufficient to conclusively evaluate myocardial performance.

Cardiac performance may also be evaluated by analyzing the timing of the first and second heart sounds. The first heart sound corresponds to the onset of ventricular systole, while the second heart sound corresponds to the onset of ventricular diastole. The first and second heart sounds can be detected using a variety of techniques, including phonocardiography, seismocardiography, and echocardiography. Out of these techniques, echocardiography is the most commonly used, but this technique requires the use of devices external to the patient.

Echocardiography may be used to obtain an index known as the myocardial performance index (MPI). The MPI is a mechanical index based on assessment of systolic and diastolic time intervals, namely, isovolumetric contraction time (ICT), isovolumetric relaxation time (IRT), and ejection time (ET). ICT is defined as the interval of left ventricular isovolumetric contraction, beginning at the end of diastole and ending at the beginning of systole. IRT is defined as the interval beginning at the end of systole and ending at the beginning of diastole. ET is the duration of systole.

Because the MPI is obtained via echocardiography, however, it is difficult to obtain the MPI using implantable devices. Generally, the MPI is obtained using devices external to the patient, limiting the ability to measure the MPI when the patient is not located at a facility with the appropriate equipment. Moreover, it is difficult to evaluate myocardial performance on a beat-by-beat basis using existing echocardiography techniques.

Multiple-chamber pacing systems are known in the art, including systems that pace and sense the right ventricle and the left ventricle. In addition, techniques associated with evaluating cardiac performance are known in the art. Table 1 lists patents that disclose pacemakers that use mechanical detection methods, such as heart sounds and accelerometers, to control pacemaker timing.

TABLE 1

| U.S. Pat. No. | Inventors | Date | Title |
| --- | --- | --- | --- |
| 5,700,283 | Salo | Dec. 23, 1997 | Method and Apparatus for Pacing Patients with Severe Congestive Heart Failure |
| 5,584,868 | Salo et al. | Dec. 17, 1996 | Cardiac Stimulating Apparatus and Method for Heart Failure Therapy |
| 5,554,177 | Kieval et al. | Sep. 10, 1996 | Method and Apparatus to Optimize Pacing Based on Intensity of Acoustic Signal |
| 5,540,727 | Tockman et al. | Jul. 30, 1996 | Method and Apparatus to Automatically Optimize the Pacing Mode and Pacing Cycle Parameters of a Dual Chamber Pacemaker |
| 5,334,222 | Salo et al. | Aug. 2, 1994 | Cardiac Stimulating Apparatus and Method for Heart Failure Therapy |
| 4,763,646 | Lekholm | Aug. 16, 1988 | Heart Pacemaker |

All patents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to cardiac pacemakers in general, and myocardial performance assessment in particular. These problems include, for example, difficulties in assessing myocardial performance on a beat-by-beat basis and the need for reliable evaluation of left ventricular performance. Various embodiments of the present invention have the object of solving at least one of the foregoing problems.

For example, it is an object of the present invention to assess myocardial performance using a combination of electrical and mechanical criteria. In particular, various embodiments of the invention assess myocardial performance by determining a QT interval based on electrogram (EGM) readings and by detecting the first and second heart sounds. The QT interval and the timing of the first and second heart sounds can then be used to evaluate certain parameters relating to myocardial performance.

In addition, it is object of the present invention to use these electrical and mechanical criteria to automatically drive therapies. For instance, the myocardial performance parameters obtained from the QT interval and from the timing of the first and second heart sounds may be used to optimize the AV delay and to optimize multisite pacing.

Some embodiments of the invention include one or more of the following features and advantages: (a) measuring myocardial performance using mechanical and electrical time intervals; (b) using T-wave and heart sounds to detect and assess myocardial performance based on ventricular pacing events; (c) using an external sound or vibration sensor to detect first and second heart sounds; (d) using internal implantable acceleration, vibration, or other sound sensors to detect acoustic signals emitted by the heart; (e) estimating myocardial performance using determined QT intervals and using the timing of the first and second heart sounds to calculate isovolumetric contraction time (ICT) and ejection time (ET) and the ratios ICT/QT and ET/QT; (f) analyzing heart sounds based on timing rather than signal amplitude; (g) automatically assessing ICT; (h) automatically estimating ET; and (i) estimating relaxation time.

Various embodiments of the present invention include methods and apparatuses for configuring heart failure pacemaker parameters based on measured QT intervals and first and second heart sounds, which correspond to mitral and aortic valve closures, respectively. Heart sounds may be detected using various internal and external techniques known in the art, including, but not limited to, accelerometers, microphones, piezoelectric sensors and transducers, and the like.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

DETAILED DESCRIPTION OF THE PREFERRED EMBODIMENTS

In the following detailed description of the preferred embodiments, reference is made to the accompanying drawings that form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
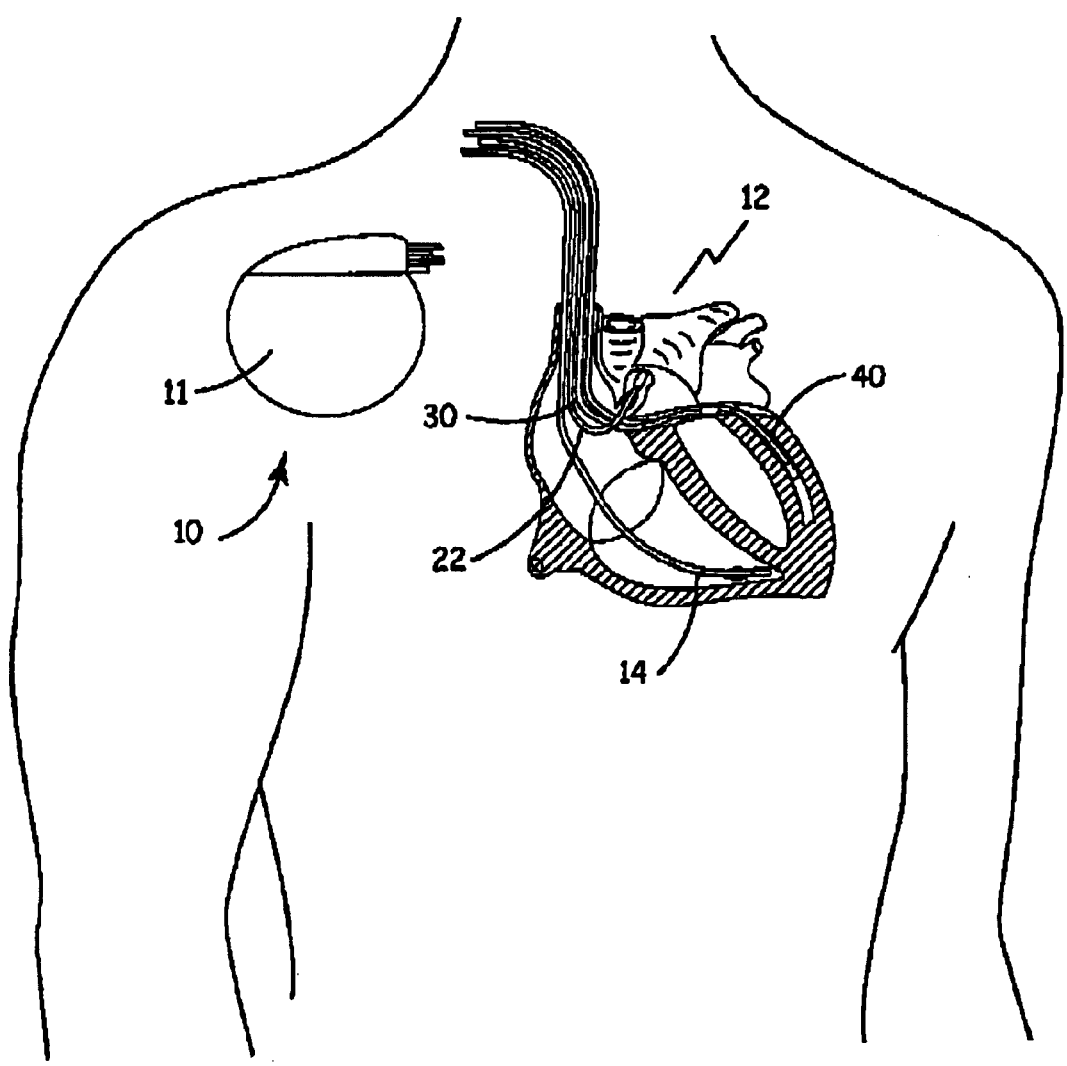
FIG. 1 is a simplified schematic view of one embodiment of an implantable medical device of the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 14, 22, 30, and 40 attached to hermetically sealed enclosure 11 and implanted near human or mammalian heart 12. Pacing and sensing leads 14, 22, 30, and 40 sense electrical signals attendant to the depolarization and re-polarization of heart 12, and further provide pacing pulses for causing depolarization of cardiac tissue in the vicinity of the distal ends thereof. Leads 14, 22, 30, and 40 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
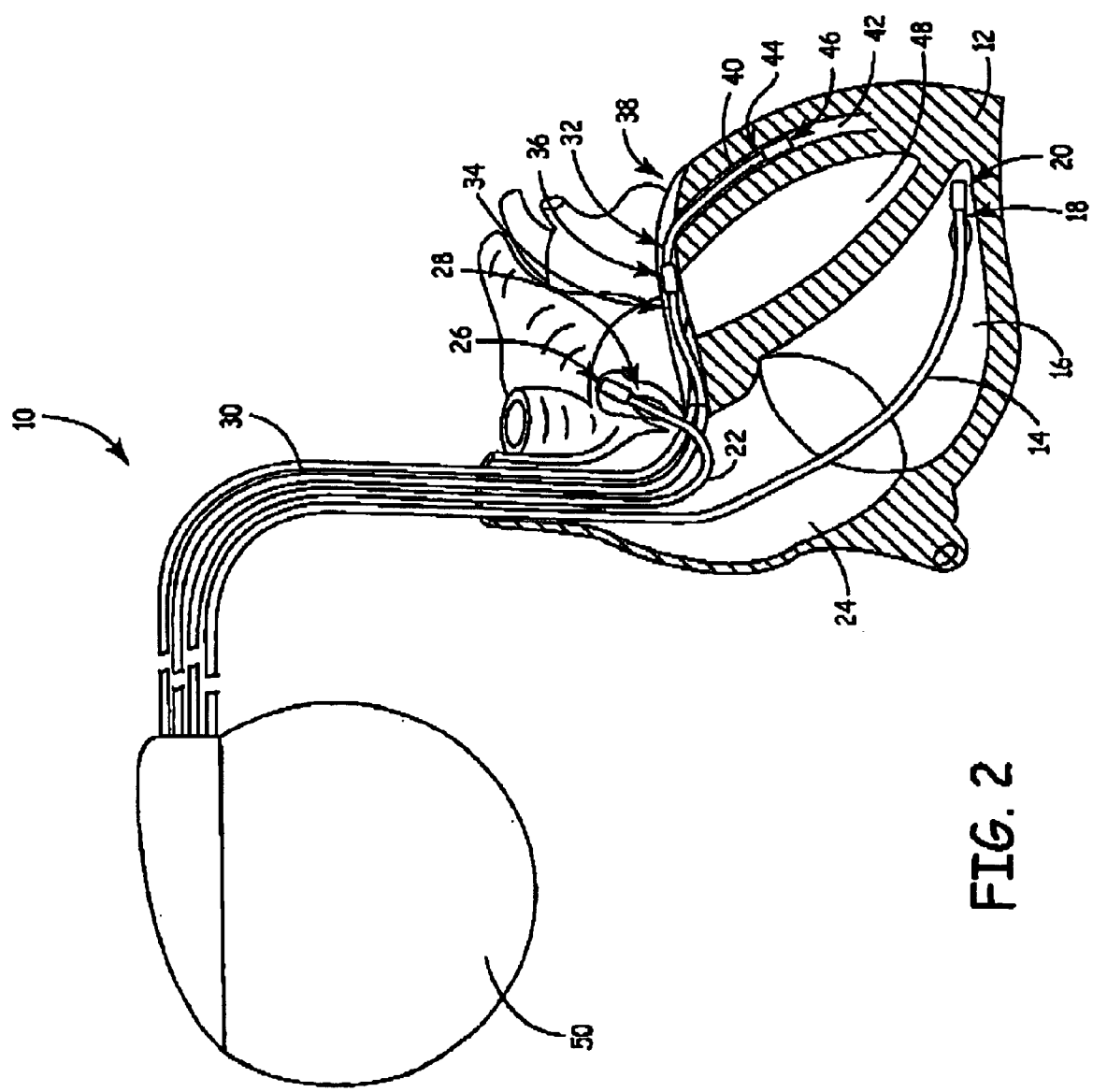
FIG. 2 is a diagram showing an example implantable medical device located in and near a heart.

FIG. 2 is a diagram illustrating an implantable medical device 10 in which the invention may be practiced. Implantable medical device 10, which is shown in conjunction with a human heart 12, comprises a four-chamber pacing system. Right ventricular pacing lead 14 is positioned conventionally in the right ventricle 16 such that its distal end is in the right ventricular apex of heart 12. Right ventricular pacing lead 14 carries bipolar electrodes 18 and 20 that sense electrical signals and can deliver pacing pulses to right ventricle 16.

Right atrial lead 22 is positioned so that its distal end is positioned within the right atrium 24. Right atrial lead 22 carries bipolar electrodes 26 and 28. Electrodes 26 and 28 sense electrical activity in right atrium 24 and may also deliver pacing pulses to right atrium 24.

Left atrial lead 30 is passed through right atrium 24 so that the distal end of lead 30 is positioned in the coronary sinus 32. Electrodes 34 and 36 on left atrial lead 30 sense electrical activity in the left atrium 38 and may also deliver pacing pulses to left atrium 38.

Left ventricular lead 40 is positioned via coronary sinus 32 in a cardiac vein 42, such as the middle or great cardiac vein. Distal electrodes 44 and 46 on left ventricular lead 40 are positioned for pacing and sensing with respect to the left ventricle 48.

Leads 14, 22, 30 and 40 are connected to a pacemaker 50 in a conventional manner. Pacemaker 50 receives electrical signals sensed by electrodes in the atria and ventricles, and may deliver pacing pulses to the atria and ventricles. In particular, pacemaker 50 receives an atrial sense from electrodes 26 or 28, and following a predetermined AV delay, delivers a bi-ventricular pace. Pacemaker 50 delivers a bi-ventricular pace by pacing right ventricle 16 and left ventricle 48 to cause cardiac resynchronization. The ventricles may be paced simultaneously, or one ventricle may be paced before the other.

Implantable medical device 10 is an exemplary device that may use the techniques of the invention. The invention is not limited to the device shown. For example, while pacemaker 50 is depicted as a four-chamber pacemaker, the invention can also be practiced in a single-chamber or dual-chamber pacemaker. Further, the invention may be practiced with unipolar electrodes rather than bipolar electrodes. The invention may further be practiced in a less complicated device, such as a device with two ventricular leads with sensing/pacing electrodes and a single atrial lead with a sensing electrode. Conversely, the invention may be practiced in a more complicated device as well, such as a device with each of the leads having more electrodes than are shown in FIG. 2.

According to various embodiments of the present invention, implantable medical device 10 detects electrical cardiac signals, including the T-wave, and calculates a QT interval based on the timing of the T-waves and of a Q-wave delivered by implantable medical device 10. In particular, the QT interval is defined as the time interval between the Q- and T-wave EGM markers. In addition, first and second heart sounds are detected, either by implantable medical device 10 or by a sensor (not shown in FIG. 2) external to implantable medical device 10 and connected to a programmer. The heart sounds may be detected using, for example, a microphone, an accelerometer, a piezoelectric sensor, or a vibration sensor. Various techniques for detecting the first and second heart sounds are described below in connection with FIGS. 7–9. The QT interval and first and second heart sounds are conceptually depicted in FIG. 5.

Figure 6:
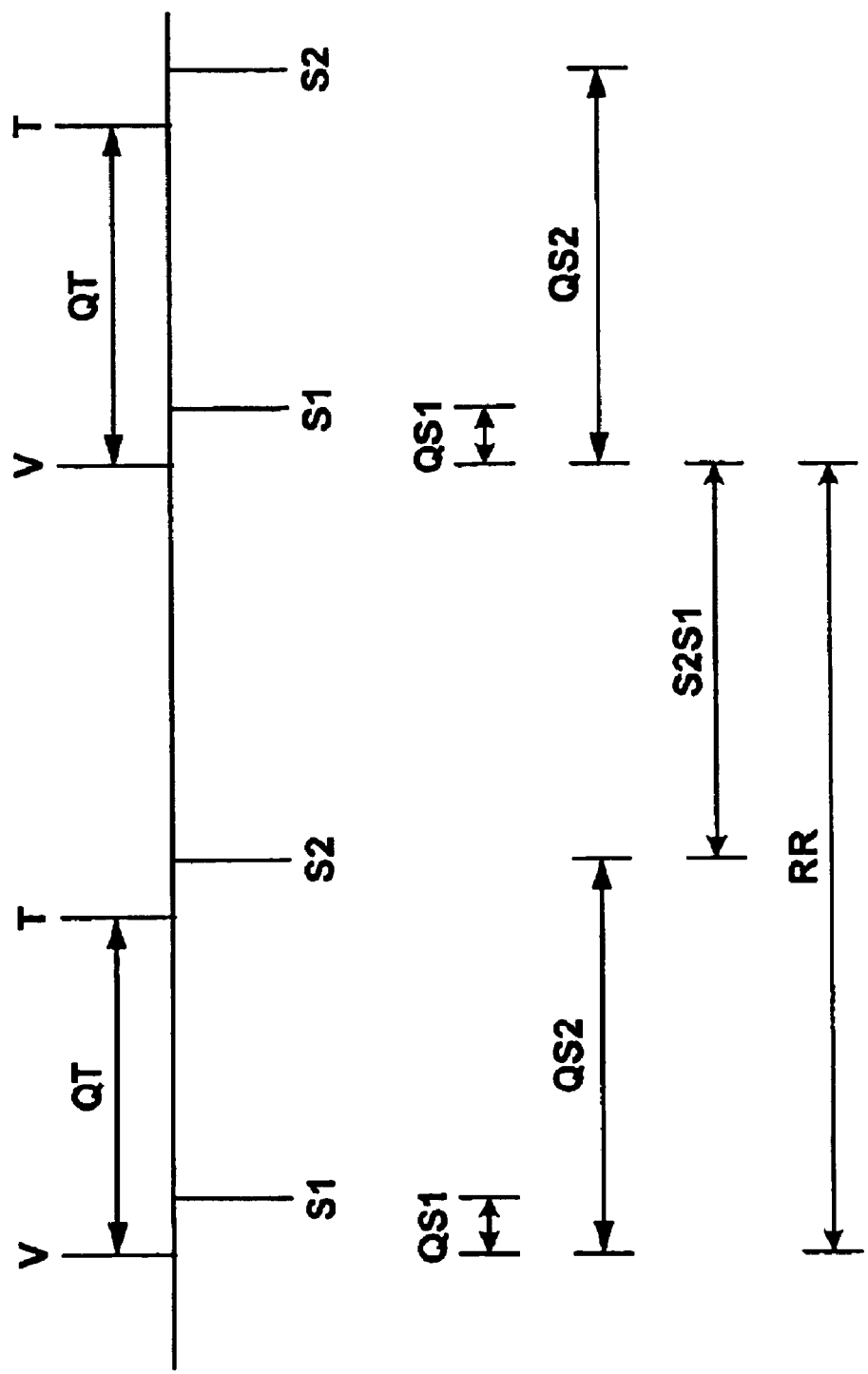
FIG. 6 is a diagram illustrating myocardial performance parameters determined according to various embodiments of the invention.

Based on the QT interval and the timing on the first and second heart sounds, implantable medical device 10 calculates various myocardial performance parameters, which are conceptually depicted in FIG. 6. These parameters may be used to derive systolic and diastolic indices of myocardial performance, described below in connection with FIG. 6. In addition, implantable medical device 10 may also calculate systolic-diastolic balance indices that reflect both systolic and diastolic performance. Implantable medical device 10 may then use these parameters and indices to configure the delivery of pacing pulses, e.g., by adjusting the delay between pacing the left and right ventricles based on myocardial performance parameters or indices as described below in connection with FIG. 10.

Figure 3:
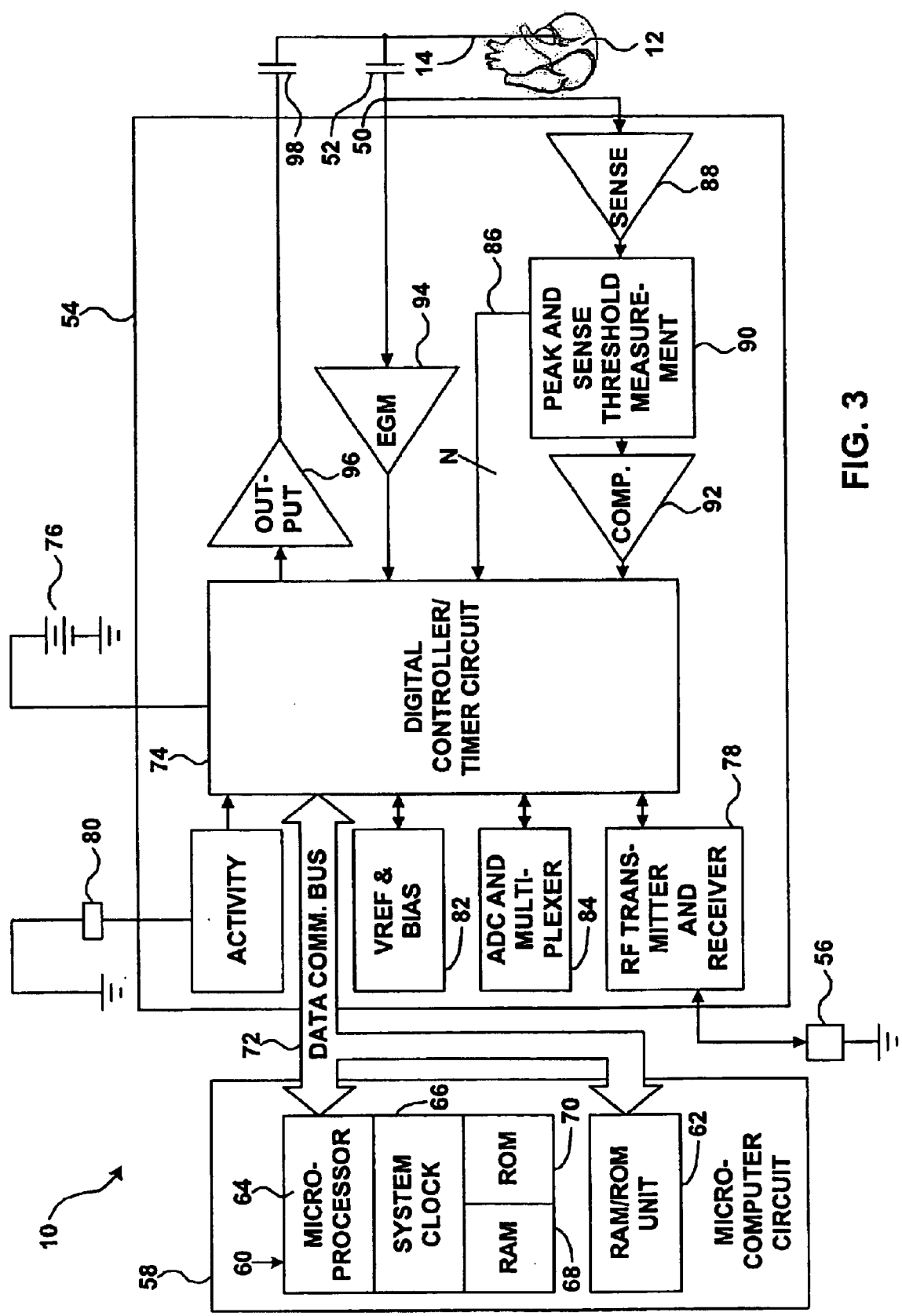
FIG. 3 is a block diagram illustrating the constituent components of the implantable medical device of FIG. 2.

FIG. 3 is a block diagram illustrating the constituent components of implantable medical device 10 in accordance with one embodiment of the present invention. Implantable medical device 10 is a pacemaker having a microprocessor-based architecture. Implantable medical device 10 is shown as including activity sensor or accelerometer 80, which is preferably a piezoceramic accelerometer bonded to a hybrid circuit located inside the housing of pacemaker 50. Accelerometer 80 typically (although not necessarily) provides a sensor output that varies as a function of a measured parameter relating to a patient's metabolic requirements. In addition, according to various embodiments of the invention, accelerometer 80 may detect first and second heart sounds for calculation of cardiac performance parameters and indices. For the sake of convenience, implantable medical device 10 in FIG. 3 is shown with lead 14 only connected thereto. However, it is understood that similar circuitry and connections not explicitly shown in FIG. 3 apply to lead 26 (shown in FIG. 2).

Implantable medical device 10 in FIG. 3 is most preferably programmable by means of an external programming unit (not shown in FIG. 3). Examples of such programmers are the commercially available Medtronic Model 9790 programmer and newer versions, which are microprocessor-based and provide a series of encoded signals to implantable medical device 10, typically through a programming head that transmits or telemeters radio frequency (RF) encoded signals to implantable medical device 10. Such a telemetry system is described in U.S. Pat. No. 5,312,453 to Wyborny et al., hereby incorporated by reference herein in its entirety. The programming methodology disclosed in the '453 patent is identified herein for illustrative purposes only. Any of a number of suitable programming and telemetry methodologies known in the art may be employed so long as the desired information is transmitted to and from the pacemaker.

As shown in FIG. 3, lead 14 is coupled to node 50 in implantable medical device 10 through input capacitor 52. Activity sensor or accelerometer 80 is most preferably attached to a hybrid circuit located inside hermetically sealed housing 42 of implantable medical device 10. The output signal provided by activity sensor 80 is coupled to input/output circuit 54. Input/output circuit 54 contains analog circuits for interfacing with heart 12, activity sensor 80, antenna 56 and circuits for the application of stimulating pulses to heart 12. The rate of heart 12 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board random access memory (RAM) 68 and read-only memory (ROM) 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of implantable medical device 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

VREF and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of implantable medical device 10 are coupled from microprocessor 64 via data bus 72 to digital controller/timer circuit 74, where digital timers and counters establish the overall escape interval of the implantable medical device 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 14. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 86 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when implantable medical device 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 12 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 12.

In some preferred embodiments of the present invention, implantable medical device 10 may operate in various non-rate-responsive modes. In other preferred embodiments of the present invention, implantable medical device 10 may operate in various rate-responsive modes. Some embodiments of the present invention are capable of operating in both non-rate-responsive and rate-responsive modes. Moreover, in various embodiments of the present invention implantable medical device 10 may be programmably configured to operate so that it varies the rate at which it delivers stimulating pulses to heart 12 in response to one or more selected sensor outputs being generated. Numerous pacemaker features and functions not explicitly mentioned herein may be incorporated into implantable medical device 10 while remaining within the scope of the present invention.

The present invention is not limited in scope to any particular number of sensors, and is not limited to pacemakers comprising activity or pressure sensors only. Although the present invention is useful in multiple-chamber pacemakers, the present invention is not limited in scope to multiple-chamber pacemakers or to pacemakers having any particular number of sensors per lead. At least some embodiments of the present invention may be applied equally well in the contexts of single-, dual-, triple- or quadruple-chamber pacemakers or other types of pacemakers. See, for example, U.S. Pat. No. 5,800,465 to Thompson et al., hereby incorporated by reference herein in its entirety, as are all U.S. Patents referenced therein.

Implantable medical device 10 may also be a pacemaker combined with a cardioverter and/or defibrillator. Various embodiments of the present invention may be practiced in conjunction with a pacemaker-cardioverter-defibrillator (PCD) such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
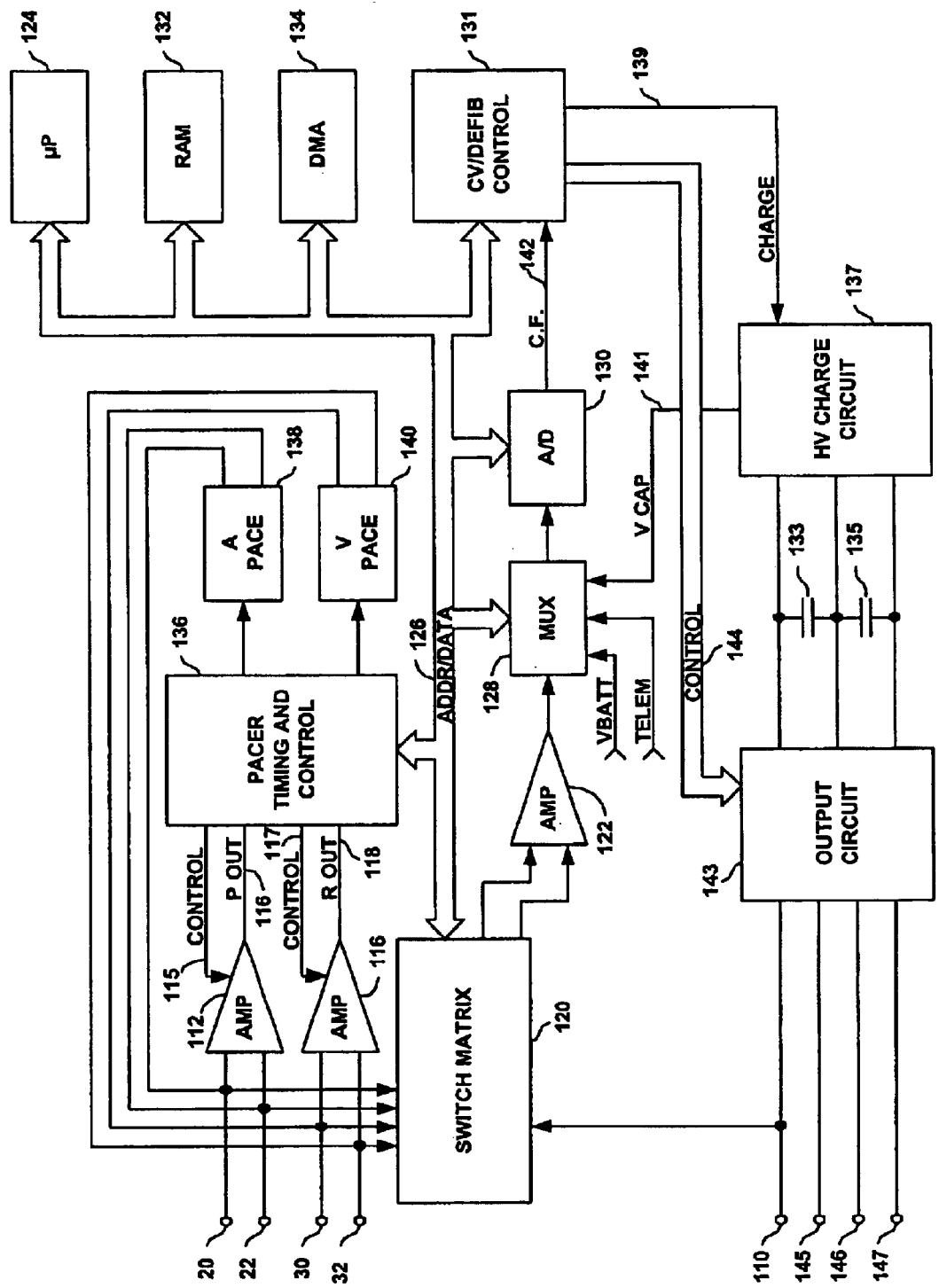
FIG. 4 is a functional schematic diagram of the implantable medical device of FIG. 2.

FIG. 4 is a functional schematic diagram of one embodiment of implantable medical device 10 of the present invention. This diagram should be taken as exemplary of the type of device in which various embodiments of the present invention may be embodied, and not as limiting, as it is believed that the invention may be practiced in a wide variety of device implementations. For example, while FIG. 4 depicts implantable medical device 10 as a pacemaker-cardioverter-defibrillator (PCD), it is believed that the invention may be practiced in cardioverters and defibrillators that do not provide anti-tachycardia pacing therapies.

Implantable medical device 10 is provided with an electrode system. Electrode 110 in FIG. 4 includes the uninsulated portion of the housing of implantable medical device 10. Electrodes 20 and 22 are located on or in left ventricle 24 of the patient and are coupled to amplifier 112, which preferably takes the form of an automatic gain controlled amplifier providing an adjustable sensing threshold as a function of the measured P-wave amplitude. A signal is generated on P out line 114 whenever the signal sensed between electrodes 20 and 22 exceeds the present sensing threshold. A control line 115 controls operation of amplifier 112.

Electrodes 30 and 32 are located on or in right ventricle 28 of the patient and are coupled to amplifier 116, which preferably also takes the form of an automatic gain controlled amplifier providing an adjustable sensing threshold as a function of the measured R-wave amplitude. A signal is generated on R out line 118 whenever the signal sensed between electrodes 30 and 32 exceeds the present sensing threshold. A control line 117 controls operation of amplifier 116. The general operation of amplifiers 112 and 116 may correspond to that disclosed in U.S. Pat. No. 5,117,824 to Keimel et al., hereby incorporated by reference herein in its entirety.

Switch matrix 120 is used to select which of the available electrodes are coupled to wide band (0.5–200 Hz) amplifier 122 for use in digital signal analysis. Selection of electrodes is controlled by microprocessor 124 via data/address bus 126, which selections may be varied as desired. Signals from the electrodes selected for coupling to bandpass amplifier 122 are provided to multiplexer 128, and thereafter converted to multi-bit digital signals by A/D converter 130, for storage in random access memory 132 under control of direct memory access (DMA) circuit 134. Microprocessor 124 may employ digital signal analysis techniques to characterize the digitized signals stored in random access memory 132 to recognize and classify the patient's heart rhythm employing any of the numerous signal processing methodologies known to the art.

The remainder of the circuitry is dedicated to the provision of cardiac pacing, cardioversion, and defibrillation therapies, and, for purposes of the present invention may correspond to circuitry known to those skilled in the art. Pacer timing/control circuitry 136 preferably includes programmable digital counters that control the basic time intervals associated with modes of pacing well known to the art. Circuitry 136 also preferably controls escape intervals associated with pacing. In the exemplary bi-ventricular pacing environment, pacer timing/control circuitry 136 controls the ventricular escape interval that is used to time pacing pulses delivered to the ventricles.

Intervals defined by pacing circuitry 136 may also include atrial pacing escape intervals, the refractory periods during which sensed P-waves and R-waves are ineffective to restart timing of the escape intervals and the pulse widths of the pacing pulses. The durations of these intervals are determined by microprocessor 124, in response to stored data in memory 132 and are communicated to pacing circuitry 136 via address/data bus 126. Pacer circuitry 136 also determines the amplitude of the cardiac pacing pulses under control of microprocessor 124.

During pacing, escape interval counters within pacer timing/control circuitry 136 may be reset upon sensing of P- and R-waves as indicated by signals on lines 114 and 118, or upon sensing of T-waves by a sense amplifier (not shown) coupled to ventricular electrodes. In accordance with the selected mode of pacing, pacer timing/control circuitry 136 triggers generation of pacing pulses by pacer output circuitry 138 and 140, which are coupled to electrodes 20, 22, 30, and 32. Escape interval counters may also be reset on generation of pacing pulses and thereby control the basic timing of cardiac pacing functions. The durations of the intervals defined by escape interval timers are determined by microprocessor 124 via data/address bus 126. The value of the count present in the escape interval counters when reset by sensed R-waves may be used to measure the durations of parameters such as R-R intervals, which measurements are stored in memory 132.

Microprocessor 124 most preferably operates as an interrupt driven device, and is responsive to interrupts from pacer timing/control circuitry 136 corresponding to the occurrence of sensed R-waves and corresponding to the generation of cardiac pacing pulses. Those interrupts are provided via data/address bus 126. Any necessary mathematical calculations to be performed by microprocessor 124 and any updating of the values or intervals controlled by pacer timing/control circuitry 136 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 124 into the pacer timing and control circuitry 136, to control the operation of the escape interval counters therein and to define refractory periods during which detection of R-waves and P-waves is ineffective to restart the escape interval counters.

Alternatively, circuitry for controlling the timing and generation of anti-tachyarrhythmia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 124 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 124 activates cardioversion/defibrillation control circuitry 131, which initiates charging of the high voltage capacitors 133 and 135 via charging circuit 137, under the control of high voltage charging control line 139. The voltage on the high voltage capacitors is monitored via VCAP line 141, which is passed through multiplexer 128 and in response to reaching a predetermined value set by microprocessor 124, results in generation of a logic signal on Cap Full (CF) line 142 to terminate charging. Thereafter, timing of the delivery of the defibrillation or cardioversion pulse is controlled by pacer timing/control circuitry 136. Following delivery of the fibrillation or tachycardia therapy microprocessor 124 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 4, delivery of cardioversion or defibrillation pulses is accomplished by output circuit 143 under the control of control circuitry 131 via control bus 144. Output circuit 143 determines whether a monophasic or biphasic pulse is delivered, the polarity of the electrodes and which of electrodes 110, 145, 146, and 147 are involved in delivery of the pulse. Output circuit 143 also includes high voltage switches that control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, implantable medical device 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 5:
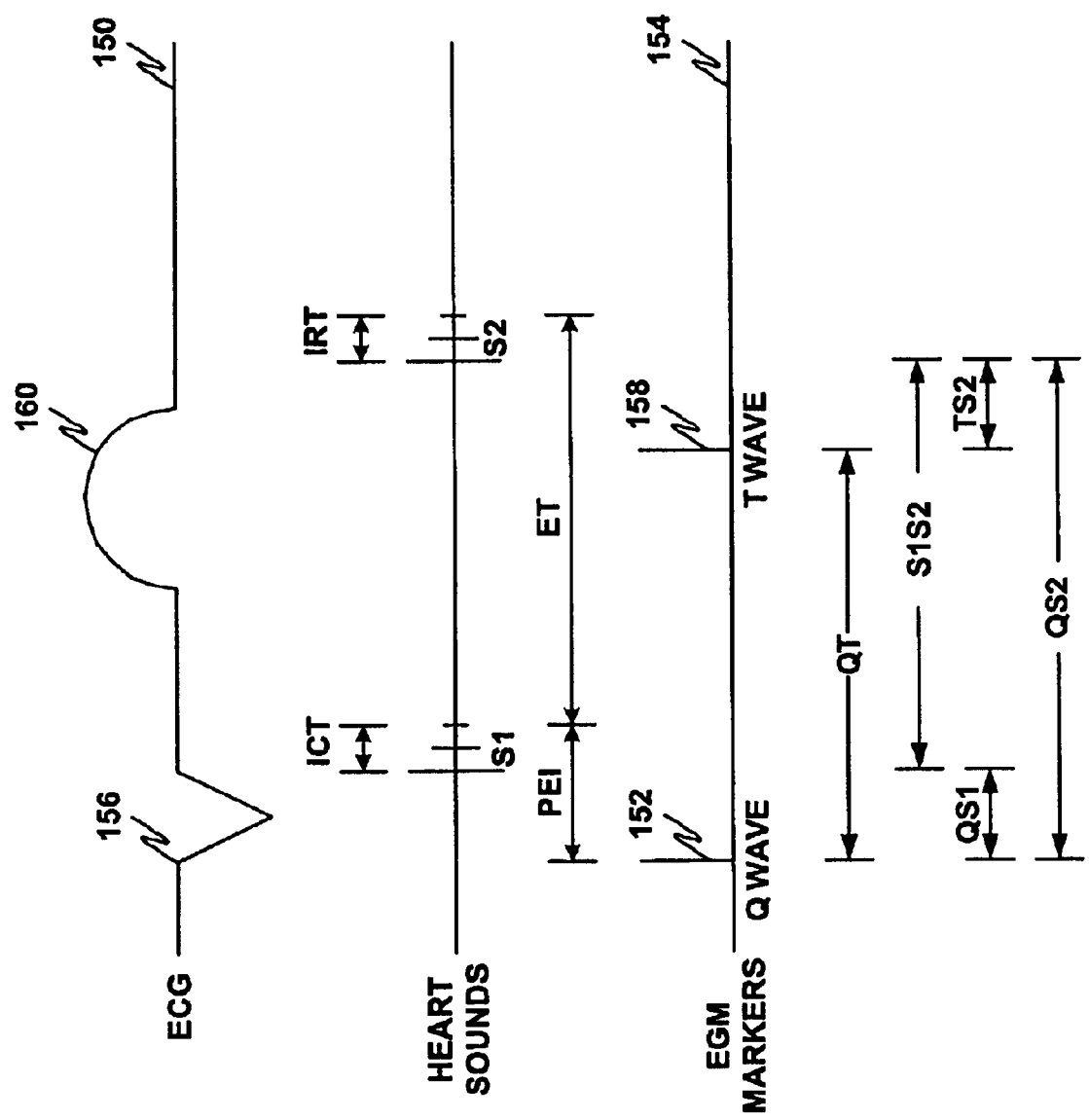
FIG. 5 is a diagram illustrating timing intervals measured according to various embodiments of the invention.

FIG. 5 is a diagram illustrating timing intervals measured according to various embodiments of the invention. Implantable medical device 10 detects T-waves and monitors delivered Q-waves based on electrocardiogram (ECG) readings 150. The timing of Q- and T-waves may be monitored, for example, by pacer timing and control circuitry 136 or by microprocessor 124. For instance, a Q-wave marker 152 on electrogram (EGM) marker channel 154 corresponds to the onset of a V-spike 156 on ECG 150. A T-wave marker 158 corresponds to a T-wave 160 on ECG 150.

Figure 7:
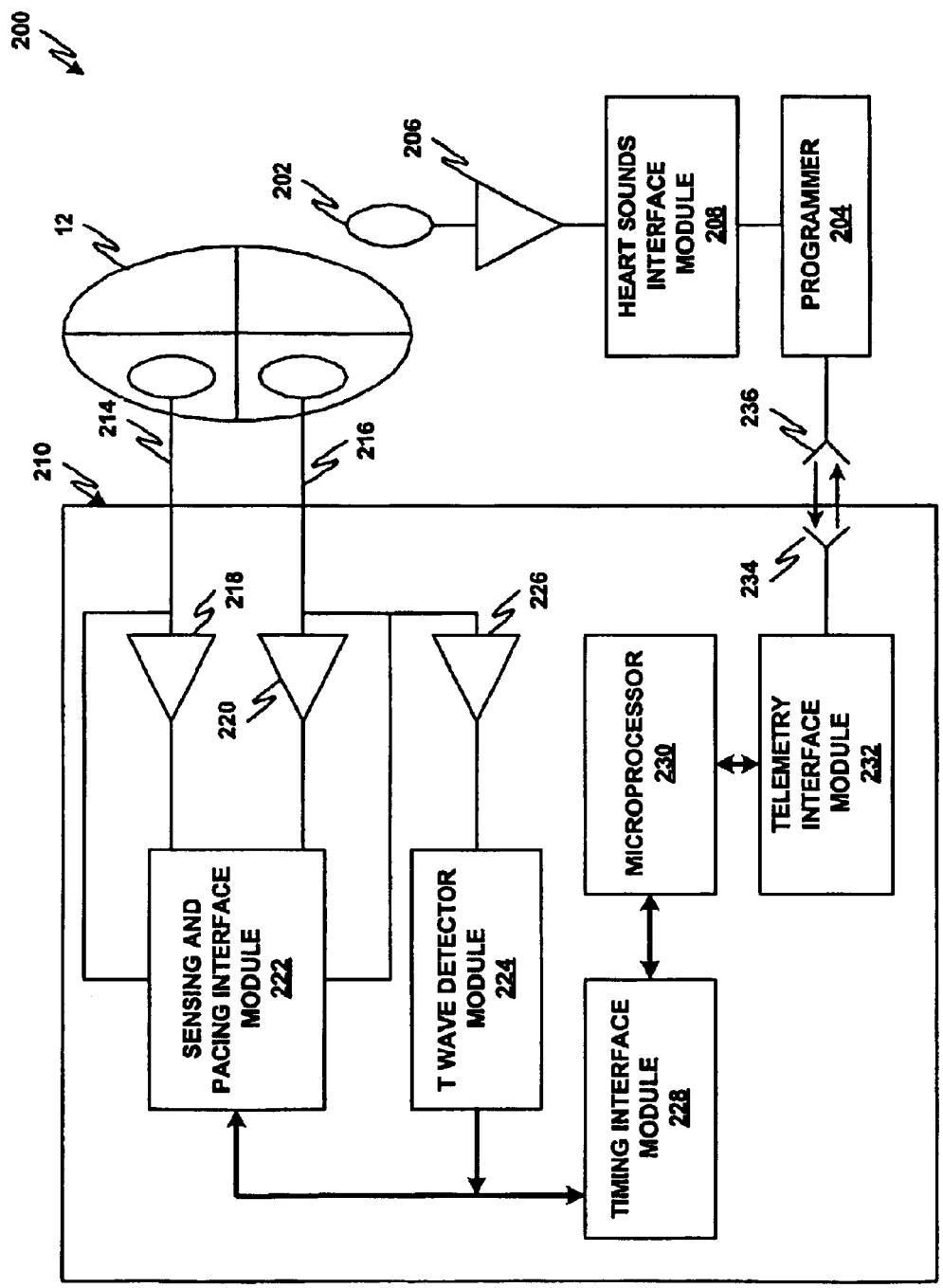
FIG. 7 is a block diagram illustrating an example medical device system according to an embodiment of the present invention.
Figure 8:
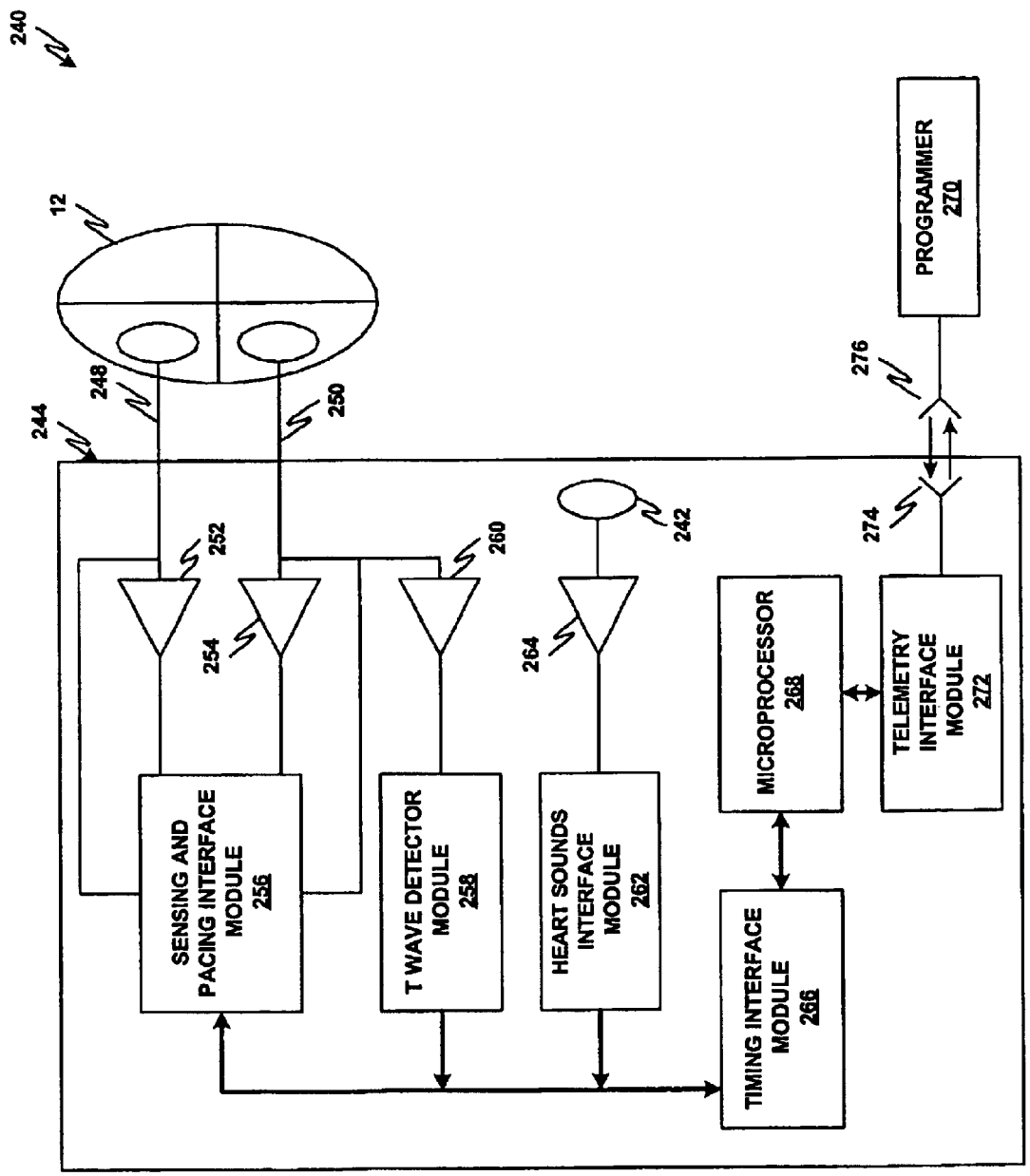
FIG. 8 is a block diagram illustrating a medical device system according to another embodiment of the present invention.
Figure 9:
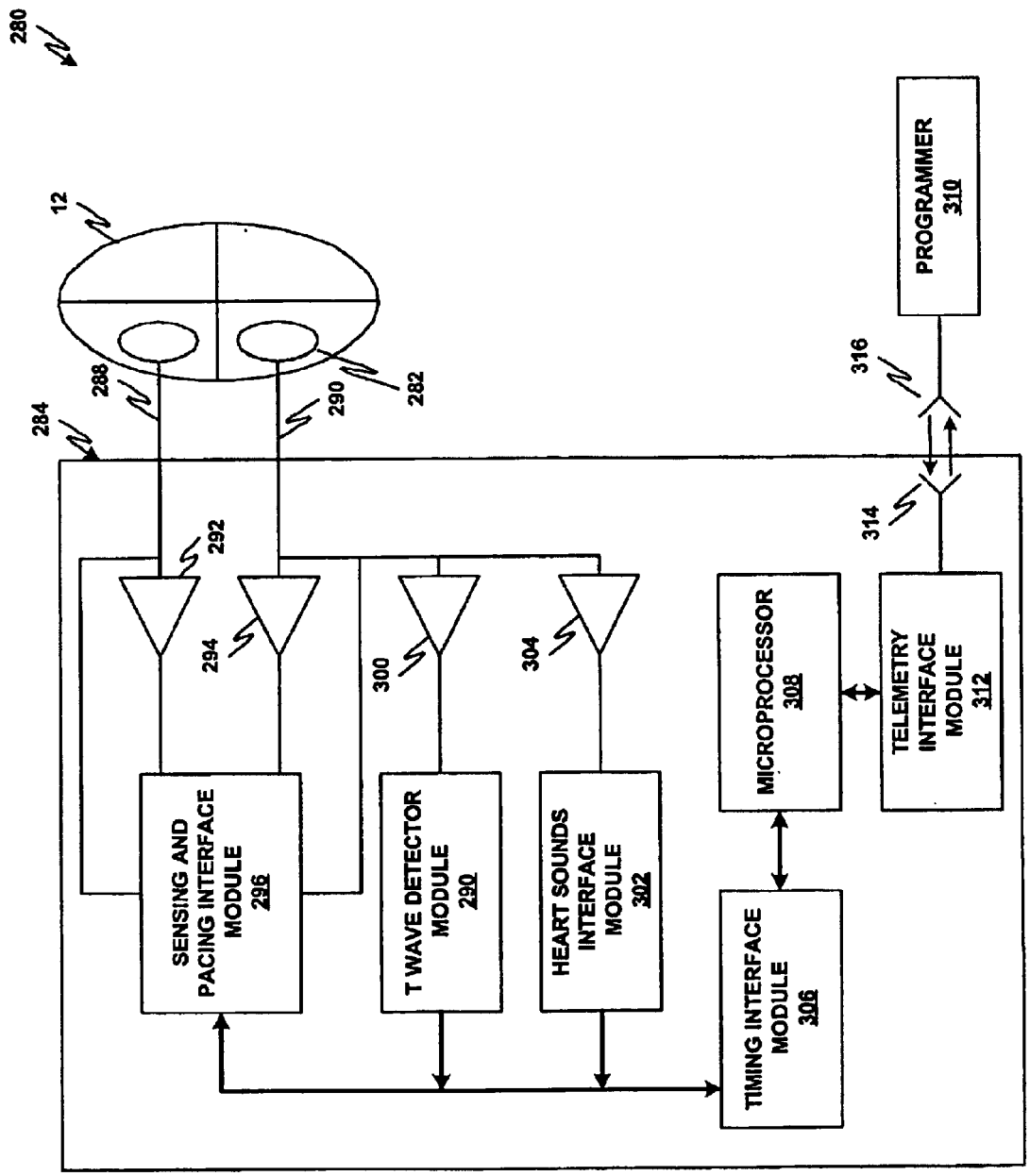
FIG. 9 is a block diagram illustrating a medical device system according to yet another embodiment of the present invention.

In addition, heart sounds S1 and S2 are also detected that correspond respectively to the onsets of ventricular systole and ventricular diastole. As described below in connection with FIGS. 7–9, the first heart sound S1 and the second heart sound S2 can be detected using any of a variety of well-known techniques, including, for example, microphones, accelerometers, vibration sensors, and piezoelectric sensors and transducers. The heart sounds S1 and S2 may be detected using a sensor external to the patient, as shown in FIG. 7, or inside the patient, as shown in FIGS. 8–9. While not required, the heart sounds S1 and S2 can be distinguished by certain traits, such as frequency. For example, the first heart sound S1 is usually soft and low-pitched, while the second heart sound S2 is generally sharper and higher-pitched. The onset of the first heart sound S1 corresponds to closure of the mitral valve, while the end of the first heart sound S1 corresponds to opening of the aortic valve. The duration of the first heart sound S1 is indicative of the isovolumetric contraction time (ICT). The onset of the second heart sound S2 corresponds to closure of the aortic valve, and the end of the second heart sound S2 corresponds to opening of the mitral valve. The duration of the second heart sound S2 indicates the isovolumetric relaxation time (IRT).

Based on the timing relationships between the Q- and T-waves and the first and second heart sounds, a number of intervals may be calculated. For example, the interval between the Q- and T-waves is defined as the QT interval. Similarly, the interval between the onset of the first heart sound S1 and the onset of the second heart sound S2 is defined as the S1S2 interval. Other intervals may be defined, e.g., a QS1 interval between the Q-wave and the onset of the first heart sound S1, a TS2 interval between the T-wave and the onset of the second heart sound S2, and a QS2 interval between the Q-wave and the onset of the second heart sound S2. A pre-ejection interval (PEI) may be defined between the Q-wave and the end of the first heart sound S1, and an ejection time (ET) may be defined between the end of the first heart sound S1 and the end of the second heart sound S2.

It should be noted that, as shown in FIG. 5, the QS1 and ICT intervals do not overlap, but are consecutive. The QS1 interval represents the interval devoted by the heart to the organization of systole, and the ICT interval represents the interval between closure of the mitral valve and opening of the aortic valve. The PEI represents the sum of the QS1 and ICT intervals.

These intervals are of particular importance to patients undergoing pacemaker therapy. Specifically, these intervals may be used for optimizing the AV delay, configuring pacing in cases of heart failure, automatically setting the upper rate limit of implantable medical device 10, and rate dependent ischemia. More generally, implantable medical device 10 may use these intervals to monitor myocardial performance. These intervals may also be used to estimate systolic- and diastolic-related parameters for determining indices of myocardial performance similar to the MPI, i.e., absolute indices of myocardial function independent of heart rate.

Evaluating myocardial performance and adjusting the operation of implantable medical device 10 according to these intervals may result in therapeutic benefits to patients. For example, in a dilated heart with mitral valve regurgitation, optimizing the AV delay with left, right, and bi-ventricular pacing can significantly reduce regurgitation. In particular, a long QS1 interval may indicate that the AV delay is too short, causing ventricular contraction while the mitral valve is still partially open and, as a result, facilitating regurgitation of blood. Accordingly, pacer timing and control circuitry 136 may react to a long QS1 interval by lengthening the AV delay, facilitating ventricular contraction only after closure of the mitral valve. The likelihood of regurgitation may be reduced as a result.

As an additional advantage, some of the intervals described above can be determined within an implantable device, without the need for external devices. Specifically, the QS1, QS2, and QT intervals can all be measured within an implantable device. By contrast, the ICT, IRT, PEI, and ET intervals are typically measured by echocardiography and are difficult or impossible to measure within an implantable device.

Instead of using the ICT and IRT to measure contraction time and relaxation time, respectively, various embodiments of the present invention instead use the QS1 and TS2 intervals. The QS1 interval is not equivalent to the ICT interval, but the QS1 interval is an indication of isovolumetric contraction time. Similarly, while the TS2 interval is not equivalent to the IRT interval, the TS2 interval does indicate the speed of relaxation. A short QS1 interval and a long S1S2 interval characterize efficient contraction, and a short TS2 interval characterizes efficient relaxation.

Moreover, measurements of the QS1, QS2, and QT intervals can be used to calculate a number of myocardial performance parameters and indices that characterize contraction and relaxation performance. FIG. 6 is a diagram that illustrates some of the performance parameters and indices that may be obtained. The designations V, T, S1, S2, and RR indicate measurements that are taken during every cardiac cycle. As described above, T, S1, and S2 denote the T-wave and the first and second heart sounds, respectively. V indicates a ventricular event, e.g., the Q-wave. RR denotes the ventricular cycle between consecutive ventricular events and is identical to the Q-Q interval.

Several parameters may be derived from the measurements of the QT, QS1, QS2, and RR intervals. For example, the S1S2 interval is the difference between the QS2 and QS1 intervals:

$$S1S2 = QS2 - QS1$$

and can serve as an estimate of the systolic interval, i.e., the ejection time (ET). Similarly, an S2S1 interval may be defined as the interval between the second heart sound of one cardiac cycle and the first heart sound of the next cardiac cycle:

$$S2S1 = RR - QS2_{present\_cycle} + QS1_{next\_cycle}$$

The S2S1 interval is a reasonable estimate of the diastolic interval, i.e., the filling time (FT). The TS2 interval may be calculated as the difference between the QS2 and QT intervals:

$$TS2 = QS2 - QT$$

As described above, a short TS2 interval indicates efficient relaxation. Another diastolic parameter is the electrical diastolic time (EDT), which can be calculated as the difference between the RR interval and the QT interval:

$$EDT = RR - QT$$

Based on these parameters, pacer timing and control circuitry 136 may calculate a number of systolic and diastolic indices indicative of myocardial performance. Systolic indices include, for example, the ratios QS1/S1S2, S1S2/QT, and QS1/QT. The ratio QS1/S1S2 represents a comparison of the isovolumetric contraction time (QS1), i.e., the time lost for ejection to the ejection time (ET), i.e., the time used for ejection. As described above, efficient contraction is characterized by a short QS1 interval and a long S1S2 interval. Accordingly, the ratio QS1/S1S2 is low in the case of efficient systole. Similarly, the ratio QS1/QT is low when systole is efficient. The ratio S1S2/QT represents a comparison of the ejection time (ET) to the electrical systolic time (QT), i.e., the time devoted to ejection. When the ratio S1S2/QT is high, a greater portion of the systole is used in ejecting blood, indicating efficient contraction.

As a particular example, if the QT interval is 300 ms and the S1S2 interval is 150 ms, the ratio S1S2/QT is 0.5, indicating that only half of the systole is devoted to ejection. The other half of the systole is lost. Accordingly, an S1S2/QT value of 0.5 indicates inefficient systole.

Diastolic indices include the ratios TS2/S2S1 and TS2/EDT. These ratios represent a comparison between the relaxation time (TS2) and the filling time (FT) and electrical diastolic time (EDT), respectively. As described above, a short TS2 interval indicates efficient relaxation. Accordingly, both ratios should be low in the case of efficient diastole.

In addition, pacer timing and control circuitry 136 may calculate indices that indicate systolic/diastolic balance and are of particular interest in evaluating the upper rate limit in paced patients and in evaluating the rate limit for patients with rate-dependent angina. Examples of systolic/diastolic balance indices include the ratios TS2/S1S2, TS2/QS1, (QS1+TS2)/S1S2, (QS1+TS2)/QT, and S1S2/S2S1. The ratios TS2/S1S2 and TS2/QS1 compare the relaxation time (TS2) to the ejection time (ET) and contraction time (QS1), respectively. The sum (QS1+TS2) represents the total isovolumetric contraction and relaxation time, i.e., the total time lost for ejection and filling. The ratios (QS1+TS2)/S1S2 and (QS1+TS2)/QT compare this lost time to the ejection time (ET) and electrical systolic time (QT), respectively. Finally, the ratio S1S2/S2S1 compares the systolic interval (S1S2) to the diastolic interval (S2S1).

FIGS. 7–9 illustrate three example configurations of medical device systems for assessing myocardial performance by analyzing systolic and diastolic time intervals, according to various embodiments of the invention.

FIG. 7 is a block diagram depicting a medical device system 200 that detects the first and second heart sounds using a sensor 202 external to the patient and connected to a programmer 204 via an amplifier 206 and a heart sounds interface module 208. Medical device system 200 includes a conventional pacemaker 210 that has endocardial leads for stimulating a heart 12. While pacemaker 210 is illustrated as a dual-chamber device, pacemaker 210 may also be implemented as a single-, or multiple-chamber device. Pacemaker 210 is connected to heart 12 via an atrial pacing/sensing electrode 214 and a ventricular pacing/sensing electrode 216. Amplifiers 218 and 220 detect the atrial and ventricular spontaneous signals, respectively, and provide this information to a sensing and pacing interface module 222, which delivers pacing pulses to the atrium and ventricle via electrodes 214 and 216.

A T-wave detector module 224 senses the endocardial T-wave through an amplifier 226. A timing interface module 228 collects information relating to paced and sensed ventricular events and to the endocardial T-wave, such as the QT and RR intervals. This information is sent to a microprocessor 230, which controls the operation of pacemaker 210 and stores programmable and diagnostic data. Microprocessor 230 transmits the information in real-time to programmer 204 via a telemetry interface 232 and antennas 234 and 236. The telemetered data includes the QT and RR intervals collected by timing interface module 228.

Programmer 204 is connected to sensor 202, which detects the first and second heart sounds. Sensor 202 may be implemented, for example, as a microphone or transducer connected to the chest of the patient in the standard position for phonocardiography or seismocardiography. Amplifier 206 and heart sounds interface module 208 are dedicated to the detection of heart sounds and transmit heart sound information, e.g., information relating to the timing of the first and second heart sounds, to a microprocessor (not shown) of programmer 204. Using the heart sound information and the telemetered data, programmer 204 calculates myocardial performance indices as described above in connection with FIGS. 5–6. A physician may use these indices to optimize pacing and drug therapies and to assess the progression of the heart disease.

Medical device system 200 may be used in conjunction with a conventional pacemaker without acoustic detection capabilities and therefore does not require replacing a pacemaker that is already implanted in a patient.

FIG. 8 is a block diagram depicting a medical device system 240 that detects the first and second heart sounds using a sensor 242 integral with the housing of a pacemaker 244 that has endocardial leads for stimulating a heart 12. While pacemaker 244 is illustrated as a dual-chamber device, pacemaker 244 may also be implemented as a single-, or multiple-chamber device. Pacemaker 244 is connected to heart 12 via an atrial pacing/sensing electrode 248 and a ventricular pacing/sensing electrode 250. Amplifiers 252 and 254 detect the atrial and ventricular spontaneous signals, respectively, and provide this information to a sensing and pacing interface module 256, which delivers pacing pulses to the atrium and ventricle via electrodes 248 and 250.

A T-wave detector module 258 senses the endocardial T-wave through an amplifier 260. In addition, sensor 242 detects the first and second heart sounds and provides information relating to detected heart sounds to a heart sounds interface module 262 via an amplifier 264. Sensor 242 may be implemented, for example, as a piezoelectric vibration sensor or an accelerometer, and may be the same sensor used for rate responsiveness. Alternatively, sensor 242 may be dedicated for detection of heart sounds. The first and second heart sounds can be identified by a time window synchronized with the V- and T-EGM markers, respectively.

A timing interface module 266 collects information relating to paced and sensed ventricular events and to the endocardial T-wave, such as the QT and RR intervals. Timing interface module 266 also collects timing information relating to the first and second heart sounds, such as the QS1 and QS2 intervals, from heart sounds interface module 262. This timing information is sent to a microprocessor 268, which controls the operation of pacemaker 244 and stores programmable and diagnostic data. Microprocessor 268 transmits the information in real-time to a programmer 270 via a telemetry interface 272 and antennas 274 and 276. The telemetered data includes the QT, RR, QS1, and QS2 intervals collected by timing interface module 266. Using the telemetered data, programmer 270 calculates myocardial performance indices as described above in connection with FIGS. 5–6. A physician may use these indices to optimize pacing and drug therapies and to assess the progression of the heart disease.

FIG. 9 is a block diagram depicting a medical device system 280 that detects the first and second heart sounds using a sensor 282 integral with an endocardial lead of a pacemaker 284. While pacemaker 284 is illustrated as a dual-chamber device, pacemaker 284 may also be implemented as a single-, or multiple-chamber device. Pacemaker 284 is connected to a heart 12 via an atrial pacing/sensing electrode 288 and a ventricular pacing/sensing electrode 290. Amplifiers 292 and 294 detect the atrial and ventricular spontaneous signals, respectively, and provide this information to a sensing and pacing interface module 296, which delivers pacing pulses to the atrium and ventricle via electrodes 288 and 290.

A T-wave detector module 298 senses the endocardial T-wave through an amplifier 300. In addition, sensor 282 detects the first and second heart sounds and provides information relating to detected heart sounds to a heart sounds interface module 302 via an amplifier 304. Sensor 282 is implemented in the tip of ventricular pacing/sensing electrode 290, and may be, e.g., a piezoelectric vibration sensor or an accelerometer. The first and second heart sounds can be identified by a time window synchronized with the V- and T-EGM markers, respectively.

A timing interface module 306 collects information relating to paced and sensed ventricular events and to the endocardial T-wave, such as the QT and RR intervals. Timing interface module 306 also collects timing information relating to the first and second heart sounds, such as the QS1 and QS2 intervals, from heart sounds interface module 302. This timing information is sent to a microprocessor 308, which controls the operation of pacemaker 284 and stores programmable and diagnostic data. Microprocessor 308 transmits the information in real-time to a programmer 310 via a telemetry interface 312 and antennas 314 and 316. The telemetered data includes the QT, RR, QS1, and QS2 intervals collected by timing interface module 306. Using the telemetered data, programmer 310 calculates myocardial performance indices as described above in connection with FIGS. 5–6. A physician may use these indices to optimize pacing and drug therapies and to assess the progression of the heart disease. In addition, pacemaker 284 can calculate the myocardial performance indices as described above and automatically adjust pacing therapies based on these indices.

Figure 10:
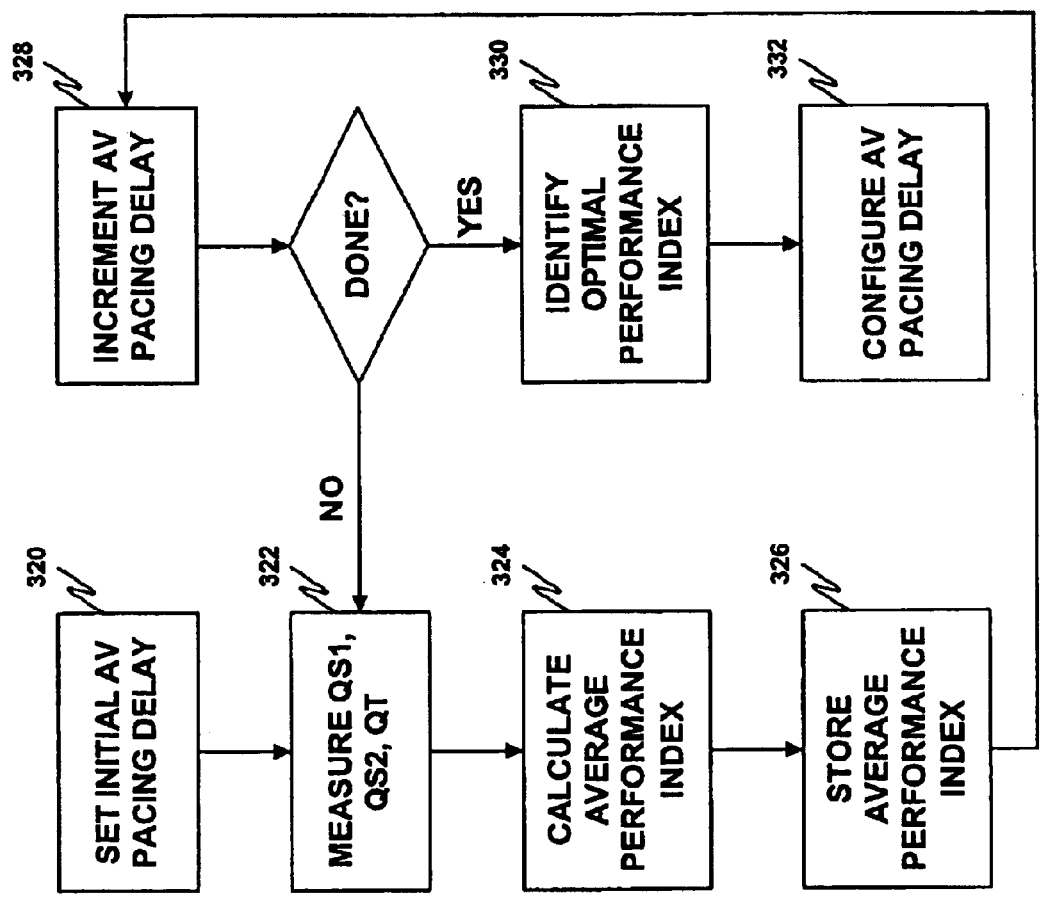
FIG. 10 is a flow diagram illustrating a therapy technique according to still another embodiment of the present invention.

The diagnostic data obtained using the techniques described above in connection with FIGS. 1–9 can be used in several types of implanted medical devices, including, but not limited to, pacemakers, defibrillators, and drug delivery systems. As a particular example, FIG. 10 depicts an example therapy technique in which the ratio QS1/S1S2 or another performance index is used to optimize the atrioventricular (AV) delay. In this technique, pacer timing and control circuitry 136 sets an initial AV delay of, for example, 60 ms (320). The parameters QS1, QS2, and QT are then measured (322) over a period of, e.g., 30 consecutive heartbeats, and a corresponding average value of QS1/S1S2, or some other performance index, is calculated over the same period (324) and stored in a memory (326).

The AV delay is then incremented (328). Myocardial performance parameters and indices are then calculated and stored for the incremented AV delay. This process repeats until a specified end of a range of AV delay values has been reached. For example, the AV delay may be incremented by steps of 20 ms to a maximum value of 300 ms.

When the end of the range has been reached, pacer timing and control circuitry 136 identifies the optimal performance index value (330) and configures therapy to the corresponding AV delay (332). The optimal performance index value may be either a maximum value or a minimum value, depending on the particular performance index used. For example, if the ratio QS1/S1S2 is used, pacer timing and control circuitry 136 configures therapy to the AV delay corresponding to the maximum value of QS1/S1S2.

Figure 11:
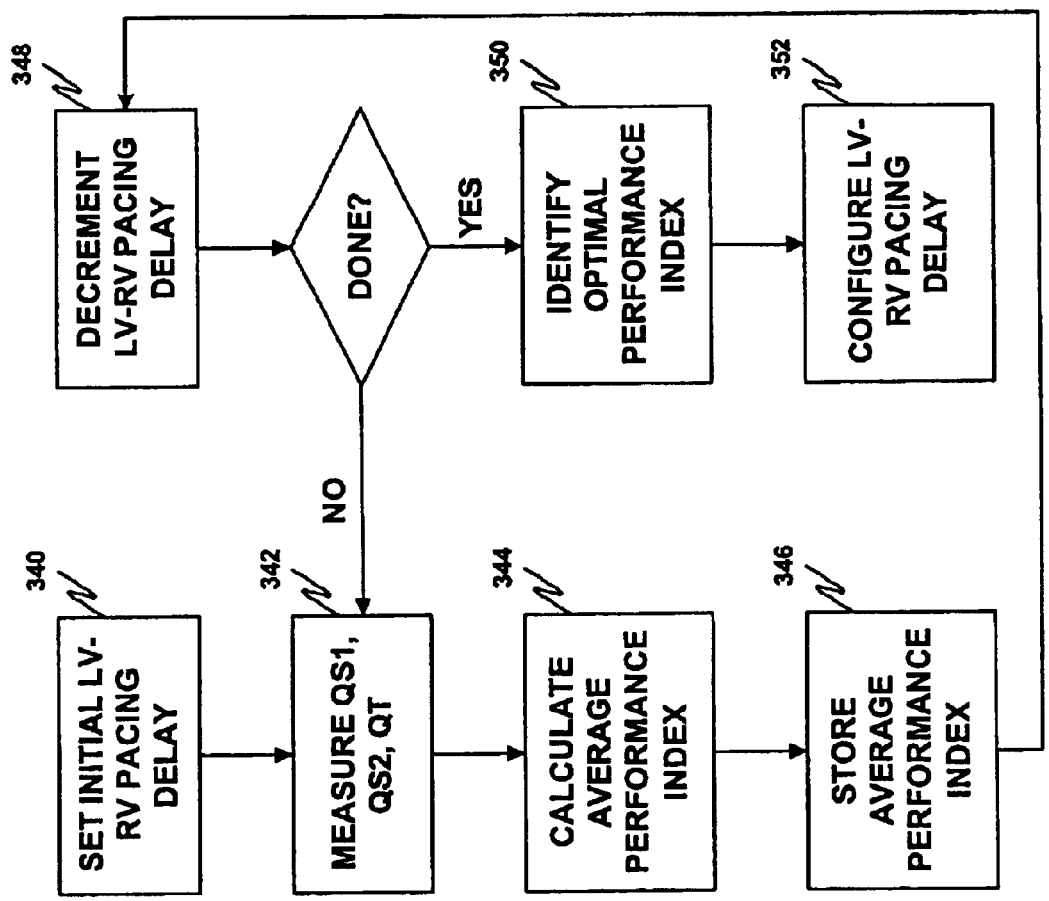
FIG. 11 is a flow diagram illustrating another therapy technique according to another embodiment of the present invention.

Other aspects of pacing can be configured using techniques similar to the technique depicted in FIG. 10. For instance, similar techniques can be used to optimize the left-right ventricular (LV-RV) pacing delay according to the maximum value of the ratio S1S2/QT, or the optimal value of another performance index. FIG. 11 depicts an example therapy technique in which the ratio S1S2/QT or another performance index is used to optimize the LV-RV delay. In this technique, pacer timing and control circuitry 136 sets an initial LV-RV delay of, for example, 50 ms (340). The parameters QS1, QS2, and QT are then measured (342) over a period of, e.g., 30 consecutive heartbeats, and a corresponding average value of S1S2/QT, or some other performance index, is calculated over the same period (344) and stored in a memory (346).

The LV-RV delay is then decremented (348). Myocardial performance parameters and indices are then calculated and stored for the decremented LV-RV delay. This process repeats until a specified end of a range of LV-RV delay values has been reached. For example, the LV-RV delay may be decremented by steps of 10 ms to a value of −50 ms. A negative LV-RV delay indicates that the RV pacing pulse precedes the LV pacing pulse.

When the end of the range has been reached, pacer timing and control circuitry 136 identifies the optimal performance index value (350) and configures therapy to the corresponding LV-RV delay (352). The optimal performance index value may be either a maximum value or a minimum value, depending on the particular performance index used. For example, if the ratio S1S2/QT is used, pacer timing and control circuitry 136 configures therapy to the LV-RV delay corresponding to the maximum value of S1S2/QT.

Figure 12:
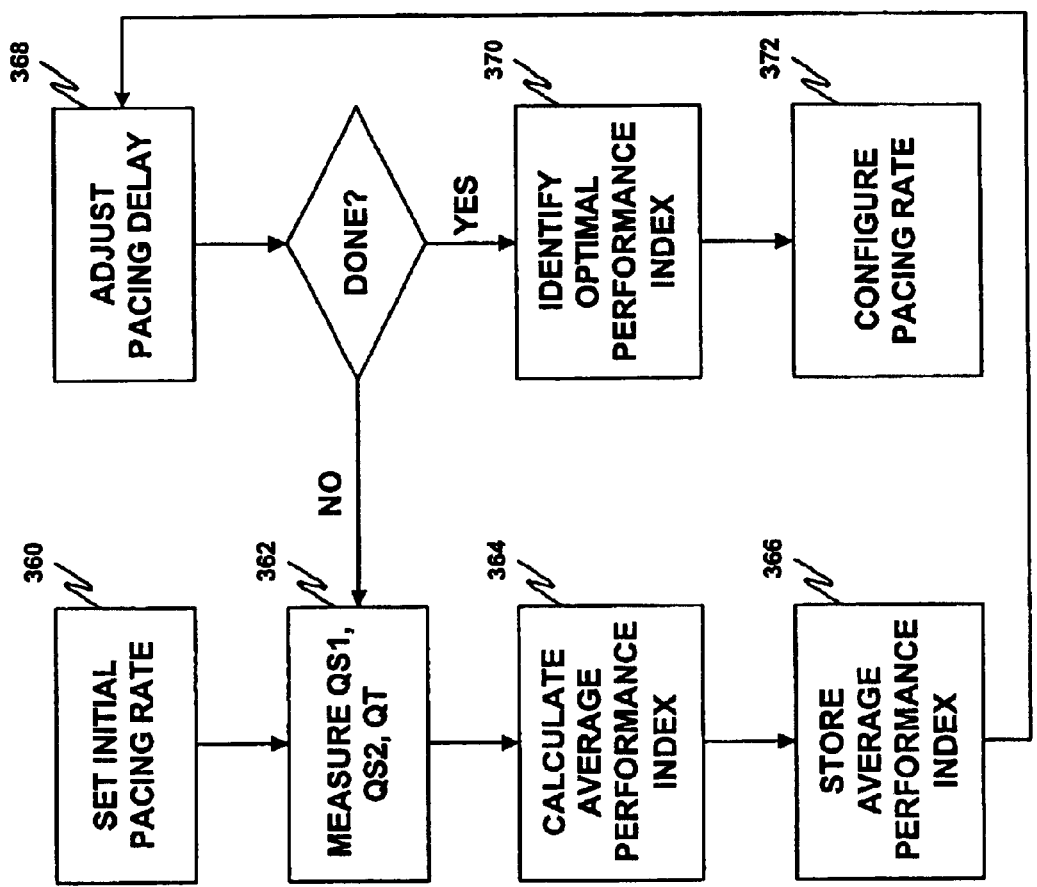
FIG. 12 is a flow diagram illustrating yet another therapy technique according to another embodiment of the present invention.

As another example, the cardiac performance parameters and indices obtained as described above can be used to optimize a pacing rate in a patient with heart failure or chronic atrial fibrillation. The optimal pacing rate varies from patient to patient and also varies within an individual patient based on, for example, the current activity level of the patient. FIG. 12 depicts an example therapy technique in which the ratio S1S2/QT or another performance index is used to optimize the pacing rate. In this technique, pacer timing and control circuitry 136 sets an initial pacing rate (360). The parameters QS1, QS2, and QT are then measured (362) over a period of, e.g., 30 consecutive heartbeats, and a corresponding average value of S1S2/QT, or some other performance index, is calculated over the same period (364) and stored in a memory (366).

The pacing rate is then adjusted, e.g., incremented or decremented (368). Myocardial performance parameters and indices are then calculated and stored for the adjusted pacing rate. This process repeats until a specified end of a range of pacing rates has been reached. For example, the pacing rate may be decremented by steps of 5 beats per second (bps) to a value of 60 bps.

When the end of the range has been reached, pacer timing and control circuitry 136 identifies the optimal performance index value (370) and configures therapy to the corresponding pacing rate (372). The optimal performance index value may be either a maximum value or a minimum value, depending on the particular performance index used. For example, if the ratio S1S2/QT is used, pacer timing and control circuitry 136 configures therapy to the pacing rate corresponding to the maximum value of S1S2/QT.

The preceding specific embodiments are illustrative of the practice of the invention. It is to be understood, therefore, that other expedients known to those skilled in the art or disclosed herein may be employed without departing from the invention or the scope of the claims. For example, the present invention is not limited to applications in which the various rates are programmed to the particular values described above. Moreover, those of skill in the art will appreciate that the invention can be made an integral part of single chamber and dual chamber pacemakers that operate in one or more of the programmed modes: AAI AAIR, VVI, VVIR, DDD, DDDR, VVI-ICD, VVIR-ICD, DDD-ICD, and/or DDDR-ICD. The present invention is also not limited to the treatment of sinus arrest and/or extreme bradycardia per se, but may find further application for facilitating post shock therapy for tachycardic arrhythmias by increasing the basic backup pacing rate immediately following defibrillation. The present invention further includes in its scope methods of making and using the implantable medical devices described hereinabove. These applications, as well as other modifications, are contemplated within the scope and spirit of the specification, drawings, abstract, and the claims that follow.

In the claims, means-plus-functions claims are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A method of cardiac pacing, the method comprising:
   detecting a first heart sound and a second heart sound;
   determining a QT interval; and
   configuring an implantable medical device as a function of the QT interval and of the first and second heart sounds by calculating a systolic index as a function of the QT interval and of the first and second heart sounds and configuring the implantable medical device as a function of the systolic index.

2. The method of claim 1, further comprising:
   calculating at least one of a systolic time, a contraction time, and an electrical systolic time as a function of the QT interval and of the first and second heart sounds; and
   calculating the systolic index as a function of at least one of the systolic time, the contraction time, and the electrical systolic time.

3. The method of claim 1, wherein configuring the implantable medical device comprises selecting at least one of a pacing rate, an atrioventricular (AV) delay, and a left ventricular-right ventricular (LV-RV) delay.

4. The method of claim 1, further comprising detecting the first and second heart sounds using a sensor external to a patient.

5. The method of claim 1, further comprising detecting the first and second heart sounds using a sensor implanted in a patient.

6. The method of claim 5, wherein the sensor is integral with the implantable medical device.

7. A method of cardiac pacing, the method comprising:
   detecting a first heart sound and a second heart sound;
   determining a QT interval; and
   configuring an implantable medical device as a function of the QT interval and of the first and second heart sounds by
      calculating a diastolic index as a function of the QT interval and of the first and second heart sounds; and
      configuring the implantable medical device as a function of the diastolic index.

8. The method of claim 7, further comprising:
   calculating at least one of a relaxation time, a diastolic time, and an electrical diastolic time as a function of the QT interval and of the first and second heart sounds; and
   calculating the diastolic index as a function of at least one of the relaxation time, the diastolic time, and the electrical diastolic time.

9. A method of cardiac pacing, the method comprising:
   detecting a first heart sound and a second heart sound;
   determining a QT interval; and
   configuring an implantable medical device as a function of the QT interval and of the first and second heart sounds by
      calculating a systolic/diastolic index as a function of the QT interval and of the first and second heart sounds; and
      configuring the implantable medical device as a function of the systolic/diastolic index.

10. The method of claim 9, further comprising:
    calculating at least one of a contraction time, a relaxation time, a systolic interval, a diastolic interval, and an electrical systolic interval as a function of the QT interval and of the first and second heart sounds; and
    calculating the systolic/diastolic index as a function of at least one of the contraction time, the relaxation time, the systolic interval, the diastolic interval, and the electrical systolic interval.

11. An implantable medical device comprising:
    a sensing arrangement to sense electrical cardiac signals;
    a pulse generator to deliver stimulation pulses to a heart; and
    a control arrangement, responsive to the sensing arrangement, to determine QT interval as a function of the electrical cardiac signals and to configure the pulse generator as a function of the QT interval and of first and second heart sounds, wherein the control arrangement is configured to calculate a systolic index as a function of the QT interval and of the first and second heart sounds and configure the pulse generator as a function of the systolic index.

12. The implantable medical device of claim 11, wherein the control arrangement is configured to:
    calculate at least one of a systolic time, a contraction time, and an electrical systolic time as a function of the QT interval and of the first and second heart sounds; and
    calculate the systolic index as a function of at least one of the systolic time, the contraction time, and the electrical systolic time.

13. The implantable medical device of claim 11, wherein the first and second heart sounds are detected using a sensor external to a patient.

14. The implantable medical device of claim 11, wherein the implantable medical device is a single-chamber cardiac pacemaker configured to operate in at least one of the group of modes consisting of AAI, AAIR, VVI, VVIR, VVI-ICD, and VVIR-ICD operational modes.

15. The implantable medical device of claim 11, wherein the implantable medical device is a dual-chamber cardiac pacemaker configured to operate in at least one of the group of modes consisting of AAI, AAIR, VVI, VVIR, DDD, DDDR, VVI-ICD, VVIR-ICD, DDD-ICD, and DDDR-ICD operational modes.

16. The implantable medical device of claim 11, further comprising an implanted acoustic sensing arrangement to detect the first and second heart sounds.

17. The implantable medical device of claim 16, wherein the implanted acoustic sensing arrangement is integral with the implantable medical device.

18. The implantable medical device of claim 16, wherein the implanted acoustic sensing arrangement comprises at least one of an accelerometer, a vibration sensor, and a piezoelectric sensor.

19. An implantable medical device comprising:

a sensing arrangement to sense electrical cardiac signals;

a pulse generator to deliver stimulation pulses to a heart; and a control arrangement, responsive to the sensing arrangement, to determine a QT interval as a function of the electrical cardiac signals and to configure the pulse generator as a function of the QT interval and of first and second heart sounds, wherein the control arrangement is configured to;

calculate a diastolic index as a function of the QT interval and of the first and second heart sounds; and configure the pulse generator as a function of the diastolic index.

20. The implantable medical device of claim 19, wherein the control arrangement is configured to:

calculate at least one of a relaxation time, a diastolic time, and an electrical diastolic time as a function of the QT interval and of the first and second heart sounds; and calculate the diastolic index as a function of at east one of the relaxation time, the diastolic time, and the electrical diastolic time.

21. An implantable medical device comprising:

a sensing arrangement to sense electrical cardiac signals;

a pulse generator to deliver stimulation pulses to a heart; and a control arrangement, responsive to the sensing arrangement, to determine a QT interval as a function of the electrical cardiac signals and to configure the pulse generator as a function of the QT interval and of first and second heart sounds, wherein the control arrangement is configured to:

calculate a systolic/diastolic index as a function of the QT interval and of the first and second heart sounds; and configure the pulse generator as a function of the systolic/diastolic index.

22. The implantable medical device of claim 21, wherein the control arrangement is configured to:

calculate at least one of a contraction time, a relaxation time, a systolic interval, a diastolic interval, and an electrical systolic interval as a function of the QT interval and of the first and second heart sounds; and calculate the systolic/diastolic index as a function of at least one of the contraction time, the relaxation time, the systolic interval, the diastolic interval, and the electrical systolic interval.

23. An implantable medical device comprising:

a sensing arrangement to sense electrical cardiac signals;

a pulse generator to deliver stimulation pulses to a heart; and a control arrangement, responsive to the sensing arrangement, to determine a QT interval as a function of the electrical cardiac signals and to configure the pulse generator as a function of the QT interval and of first and second heart sounds, wherein the control arrangement is configured to select at least one of a pacing rate, an atrioventricular (AV) delay, and a left ventricular-right ventricular (LV-RV) pacing delay.

24. A medical device System comprising:

an electrical sensing arrangement to sense electrical cardiac signals;

an acoustic sensing arrangement to sense first and second heart sounds;

a pulse generator to deliver stimulation pulses to a heart;

at least one pacing lead, coupled to the pulse generator and configured to deliver the stimulation pulses to a chamber of the heart; and a control arrangement, responsive to the sensing arrangement and configured to determine a QT interval as a function of the electrical cardiac signals and to cause the pulse generator to deliver the stimulation pulses at a rate determined as a function of the QT interval and of the first and second heart sound, wherein the control arrangement is configured to:

calculate a systolic index as a function of the QT interval and of the first and second heart sounds; and configure the pulse generator as a function of the systolic index.

25. The medical device system of claim 24, wherein the control arrangement is configured to:

calculate at least one of a systolic time, a contraction time, and an electrical systolic time as a function of the QT interval and of the first and second heart sounds; and calculate the systolic index as a function of at least one of the systolic time, the contraction time, and the electrical systolic time.

26. The medical device system of claim 24, wherein the control arrangement is configured to select at least one of a pacing rate, an atrioventricular (AV) delay, and a left ventricular-right ventricular (LV-RV) pacing delay.

27. The medical device system of claim 24, wherein the acoustic sensing arrangement is coupled to a programming arrangement external to a patient.

28. The medical device system of claim 24, wherein the medical device system comprises a single-chamber cardiac pacemaker configured to operate in at least one of the group of modes consisting of AAI, AAIR, VVI, VVIR, VVI-ICD, and VVIR-ICD operational modes.

29. The medical device system of claim 24, wherein the medical device system comprises a dual-chamber cardiac pacemaker configured to operate in at least one of the group of modes consisting of AAI, AAIR, VVI, VVIR, DDD, DDDR, VVI-ICD, VVIR-ICD, DDD-ICD, and DDDR-ICD operational modes.

30. The medical device system of claim 24, further comprising a programming arrangement to program the control arrangement.

31. The medical device system of claim 30, wherein the programming arrangement comprises a microprocessor to provide an encoded signal to the control arrangement.

32. The medical device system of claim 24, wherein the acoustic sensing arrangement is implanted in a patient.

33. The medical device system of claim 32, wherein the acoustic sensing arrangement is integral with an implantable medical device.

34. The medical device system of claim 32, wherein the acoustic sensing arrangement comprises at least one of an accelerometer, a vibration sensor, and a piezoelectric sensor.

35. A medical device system comprising:

an electrical sensing arrangement to sense electrical cardiac signals;

an acoustic sensing arrangement to sense first and second heart sounds;

a pulse generator to deliver stimulation pulses to a heart;

at least one pacing lead, coupled to the pulse generator and configured to deliver the stimulation pulses to a chamber of the heart; and a control arrangement, responsive to the sensing arrangement and configured to determine a QT interval as a function of the electrical cardiac signals and to cause the pulse generator to deliver the stimulation pulses at a rate determined as a function of the QT interval and of the first and second heart sounds, wherein the control arrangement is configured to:
  calculate a diastolic index an a function of the QT interval and of the first and second heart sounds; and
  configure the pulse generator as a function of the diastolic index.

36. The medical device system of claim 35, wherein the control arrangement is configured to:
  calculate at least one of a relaxation time, a diastolic time, and an electrical diastolic time as a function of the QT interval and of the first and second heart sounds; and
  calculate the diastolic index as a function of at least one of the relaxation time, the diastolic time, and the electrical diastolic time.

37. A medical device system comprising:
  an electrical sensing arrangement to sense electrical cardiac signals;
  an acoustic sensing arrangement to sense first and second heart sounds;
  a pulse generator to deliver stimulation pulses to a heart;
  at least one pacing lead, coupled, to the pulse generator and configured to deliver the stimulation pulses to a chamber of the heart; and
  a control arrangement, responsive to the sensing arrangement and configured to determine a QT interval as a function of the electrical cardiac signals and to cause the pulse generator to deliver the stimulation pulses at a rate determined as a function of the QT interval and of the first and second heart sounds, wherein the control arrangement is configured to:
  calculate a systolic/diastolic index as a function of the QT interval and of the first and second heart sounds; and
  configure the pulse generator as a function of the systolic/diastolic index.

38. A The medical device system of claim 37, wherein the control arrangement is configured to:
  calculate at least one of a contraction time, a relaxation time, a systolic interval, a diastolic interval, and an electrical systolic interval as a function of the QT interval and of the first and second heart sounds; and
  calculate the systolic/diastolic index as a function of at least one of the contraction time, the relaxation time, the systolic interval, the diastolic interval, and the electrical systolic interval.

39. A method of manufacturing an implantable medical device comprising:
  providing a sensing arrangement to sense electrical cardiac signals;
  providing a pulse generator to deliver stimulation pulses to a heart;
  coupling a control arrangement to the sensing arrangement; and
  programming the control arrangement to determine a QT interval as a function of the electrical cardiac signals and to configure the pulse generator as a function of the QT interval and of first and second heart sounds, to calculate a systolic index as a function of the QT interval and of the first and second heart sounds, and to configure the pulse generator as a function of the systolic index.

40. The method of manufacturing an implantable medical device of claim 39, further comprising programming the control arrangement to:
  calculate at least one of a systolic time, a contraction time, and an electrical systolic time as a function of the QT interval and of the first and second heart sounds; and
  calculate the systolic index as a function of at least one of the systolic time, the contraction time, and the electrical systolic time.

41. The method of manufacturing an implantable medical device of claim 39, comprising programming the control arrangement to select at least one of a pacing rate, an atrioventricular (AV) delay, and a left ventricular-right ventricular (LV-RV) pacing delay.

42. The method of manufacturing an implantable medical device of claim 39, further comprising configuring the implantable medical device to operate in at least one of the group of modes consisting of AAI, AAIR, VVI, VVIR, DDD, DDDR, VVI-ICD, VVIR-ICD, DDD-ICD, and DDDR-ICD operational modes.

43. The method of manufacturing an implantable medical device of claim 39 further comprising providing an implanted acoustic sensing arrangement to detect the first and second heart sounds.

44. The method of manufacturing an implantable medical device of claim 43, wherein the implanted acoustic sensing arrangement is integral with the implantable medical device.

45. The method of manufacturing an implantable medical device of claim 43, wherein the implanted acoustic sensing arrangement comprises at least one QT an accelerometer, a vibration sensor, and a piezoelectric sensor.

46. The method of manufacturing an implantable medical device of claim 45, wherein the first and second heart sounds are detected using a sensor external to a patient.

47. A method of manufacturing an implantable medical device comprising:
  providing a sensing arrangement to sense electrical cardiac signals;
  providing a pulse generator to deliver stimulation pulses to a heart;
  coupling a control arrangement to the sensing arrangement; and
  programming the control arrangement to determine a QT interval as a function of the electrical cardiac signals and to configure the pulse generator as a function of the QT interval and of first and second heart sounds, to
  calculate a diastolic index as a function of the QT interval and of the first and second heart sounds, and to
  configure the pulse generator as a function of the diastolic index.

48. The method of manufacturing an implantable medical device of claim 47, further comprising programming the control arrangement to:
  calculate at least one of a relaxation time, a diastolic time, and an electrical diastolic time as a function of the QT interval and of the first and second heart sounds; and
  calculate the diastolic index as a function of at least one of the relaxation time, the diastolic time, and the electrical diastolic time.

49. A method of manufacturing an implantable medical device comprising:
  providing a sensing arrangement to sense electrical cardiac signals;

providing a pulse generator to deliver stimulation pulses to a heart;

coupling a control arrangement to the sensing arrangement; and programming the control arrangement to determine a QT interval as a function of the electrical cardiac signals and to configure the pulse generator as a function of the QT interval and of first and second heart sounds, to calculate a systolic/diastolic index as a function of the QT interval and of the first and second heart sound, and to configure the pulse generator as a function of the systolic/diastolic index.

50. The method of manufacturing an implantable medical device of claim 49, further comprising programming the control arrangement to:

calculate at least one of a contraction time, a relaxation time, a systolic interval, a diastolic interval, and an electrical systolic interval as a function of the QT interval and of the first and second heart sounds; and calculate the systolic/diastolic index as a function of at least one of the contraction time, the relaxation time, the systolic interval, the diastolic interval, and the electrical systolic interval.

* * * * *

UNITED STATES PATENT AND TRADEMARK OFFICE
CERTIFICATE OF CORRECTION

PATENT NO. : 6,792,308 B2
DATED : September 14, 2004
INVENTOR(S) : Giorgio Corbucci It is certified that error appears in the above-identified patent and that said Letters Patent is hereby corrected as shown below:

Column 21,
Line 21, delete "at east one" and insert -- at least one --.

Column 22,
Line 10, delete "heart sound," and insert -- heart sounds --.

Signed and Sealed this

Twenty-fourth Day of May, 2005

JON W. DUDAS
*Director of the United States Patent and Trademark Office*